United States Patent
Hiranaka et al.

(10) Patent No.: US 8,508,738 B2
(45) Date of Patent: Aug. 13, 2013

(54) NITROGEN OXIDE SENSING ELEMENT, NITROGEN OXIDE SENSOR, NITROGEN OXIDE CONCENTRATION DETERMINATION DEVICE USING SAME, AND METHOD FOR DETERMINING NITROGEN OXIDE CONCENTRATION

(75) Inventors: Kouichi Hiranaka, Ehime (JP); Toyofumi Nagamatsu, Ehime (JP); Yoshihiko Sadaoka, Ehime (JP); Yoshiteru Itagaki, Ehime (JP)

(73) Assignee: Panasonic Corporation, Osaka (JP)

( * ) Notice: Subject to any disclaimer, the term of this patent is extended or adjusted under 35 U.S.C. 154(b) by 169 days.

(21) Appl. No.: 13/131,200

(22) PCT Filed: Nov. 6, 2009

(86) PCT No.: PCT/JP2009/005891
§ 371 (c)(1),
(2), (4) Date: May 25, 2011

(87) PCT Pub. No.: WO2010/061536
PCT Pub. Date: Jun. 3, 2010

(65) Prior Publication Data
US 2011/0228276 A1    Sep. 22, 2011

(30) Foreign Application Priority Data

Nov. 26, 2008   (JP) ................. 2008-300265
Jun. 24, 2009   (JP) ................. 2009-149241

(51) Int. Cl.
*G01N 21/00*    (2006.01)
(52) U.S. Cl.
USPC ........................................ 356/437

(58) Field of Classification Search
USPC ........................................ 356/437
See application file for complete search history.

(56) References Cited

U.S. PATENT DOCUMENTS 5,582,170 A  * 12/1996 Soller .................... 600/322
6,096,557 A    8/2000 Tanaka et al.

(Continued)

FOREIGN PATENT DOCUMENTS

EP        0733901       9/1996
JP        05-505871     8/1993

(Continued)

OTHER PUBLICATIONS

Gulino et al., "$NO_2$ sensing ability of a monolayer of cobalt(II) porphyrin molecules covalently assembled on a engineered silica substrate," Inorganica Chimica Acta, 2008, vol. 361, pp. 3877-3881.

(Continued)

*Primary Examiner* — Tu Nguyen
(74) *Attorney, Agent, or Firm* — Hamre, Schumann, Mueller & Larson, P.C.

(57) ABSTRACT

The nitrogen oxide sensing element of the present invention is such that a sensing film (11) is formed on the surface of a substrate (12a), the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal; thus, this sensing element is capable of determining the concentration of NO with high sensitivity and satisfactory accuracy under the condition that the cobalt porphyrin is not affected by reaction inhibitors such as $O_2$ and CO even in the atmosphere.

13 Claims, 23 Drawing Sheets

(56) References Cited

U.S. PATENT DOCUMENTS

| | | | |
|---|---|---|---|
| 6,183,709 B1 * | 2/2001 | Stephenson et al. | ....... 423/213.2 |
| 6,230,545 B1 | 5/2001 | Adolph et al. | |
| 6,495,102 B1 | 12/2002 | Suslick et al. | |
| 6,893,716 B2 * | 5/2005 | McGimpsey et al. | ......... 428/333 |
| 2006/0289313 A1 | 12/2006 | Yuasa et al. | |

FOREIGN PATENT DOCUMENTS

| | | |
|---|---|---|
| JP | 5-312709 | 11/1993 |
| JP | 6-093444 | 4/1994 |
| JP | 9-171011 | 6/1997 |
| JP | 11-153545 | 6/1999 |
| JP | 2002-085969 | 3/2002 |
| WO | 91/07659 | 5/1991 |
| WO | 02/057738 | 7/2002 |
| WO | 2004/074828 | 9/2004 |

OTHER PUBLICATIONS

Arai et al., "Optical detection of nitrogen monoxide by metal porphine dispersed in amorphous silica film," Chemistry Letters, 1988, pp. 521-524.

Miyamoto et al., "Nitrogen monoxide adsorption and contact decomposition properties of Co (II) complexes," Journal of the Chemical Society of Japan, 1998, No. 5, pp. 338-345 (English language abstract provided).

* cited by examiner

NITROGEN OXIDE SENSING ELEMENT, NITROGEN OXIDE SENSOR, NITROGEN OXIDE CONCENTRATION DETERMINATION DEVICE USING SAME, AND METHOD FOR DETERMINING NITROGEN OXIDE CONCENTRATION

TECHNICAL FIELD

The present invention relates to a nitrogen oxide sensor.

BACKGROUND ART

Since nitrogen monoxide (hereinafter, referred to as NO) was found as the essential component of a muscle relaxant factor, the physiological effect of NO has been elucidated, and hence NO can be used as a neural information transmitter or an infection marker.

In particular, the analysis of the NO gas in the exhaled air has been attracting attention as a marker for nowadays continuously increasing respiratory tract infection, due to asthma or allergy. Such analysis has been also attracting attention because of the capability of noninvasive diagnosis of disease without imposing burden on patients. The NO gas concentration in the exhaled air is 2 ppb to 20 ppb in normal subjects, but is known to increase by a factor of about three in the cases of respiratory tract inflammation such as allergy and asthma. Therefore, the determination of the NO gas in the exhaled air can be utilized for the determination of degree of inflammation of the respiratory tract of a patient or for asthma care guidelines such as the determination of dosage of therapeutic medicine for asthma.

Conventionally, the method for determining NO, to be applied to the exhaled air, has been such that NO collected from the exhaled air of a patient is allowed to react with ozone under reduced pressure, and light emitted during the reaction is detected. However, this chemiluminescence method requires expensive peripheral devices such as an ozone generating device, and the maintenance of such devices is laborious.

Under such circumstances, in order that an asthma patient may determine the NO concentration everyday at a hospital or at home to perform self-administration of asthma, there is a demand for a NO analyzer which is inexpensive, compact, excellent in gas selectivity and high in sensitivity.

Recently, there has been disclosed a method in which a cobalt tetrasulfothienyl porphyrin (hereinafter, referred to as Co{T(5-ST)P}) supported on sol-gel silica is reacted with NO in a vacuum chamber, and NO coordinated to Co{T(5-ST)P} is detected by spectroscopic measurement (see, for example, Non Patent Literature 1).

In this method, the Co{T(5-ST)P} supported on the surface of the sol-gel silica was heated to 200° C. for the purpose of attaining a difference between the reactivity of the nitrogen oxide gas and the reactivity of other gases, and thus 17 ppm of the NO gas was successfully sensed.

There has also been developed a NO sensor in which $Ga_2O_3$ is formed by oxidation of Ga on a GaAs field effect transistor, then a monomolecular film of hematoporphyrin IX, protoporphyrin IX, hemin, or cobalt phorphyrin II chloride is formed on the $Ga_2O_3$, and the monomolecular film is beforehand provided with a gate potential and is reacted with NO, and from the thus generated electric current change, a NO concentration is determined (see, for example, Patent Literature 1).

There has also been known a method in which in a vacuum chamber, a cobalt tetraphenylporphyrin (5,10,15,20-tetraphenyl-21H,23H-porphyrin cobalt (hereinafter, referred to as CoTPP)) and NO are reacted with each other, and the NO coordinated to the CoTPP is detected by infrared spectroscopic measurement (see, for example, Non Patent Literature 2).

There has also been disclosed a method in which a temperature controller formed of indium tin oxide is provided on the backside of a substrate for the purpose of improving reproducibility, a film containing a benzotriazaporphyrin incorporating a transition metal such as chromium ($Cr^{3+}$), vanadyl (VO), manganese (Mn), cobalt (Co) and copper (Cu) is formed on the surface of the substrate to fabricate a gas sensor, and the gas sensor is preheated before the sensor is exposed to a gas. The sensor is preheated at 130° C., and the reactivity to a chlorine gas of 250 ppm to 100% in concentration has been measured with a conductivity change. The preheating effect on sensor recovery is as follows: in the case of nonpreheating treatment, the sensor recovery takes 24 hours after the exposure to the gas; in the case of a preheating temperature of 190° C., the sensor is recovered in 4 minutes; with the preheating at such a high temperature of 190° C., the second and later runs of exposure undergo a gradual decrease in the change magnitude of the sensor with respect to a chlorine gas, and thus the sensor is degraded (see, for example, Patent Literature 2).

There has also been disclosed a volatile gas detection method which disposes, for the purpose of determining VOC gas components, a plurality of porphyrins selected from the group consisting of porphyrins each adopting, as a porphyrin central metal, tin ($Sn^{4+}$), cobalt ($Co^{3+}$ or $Co^{2+}$), chromium ($Cr^{3+}$), iron ($Fe^{3+}$), ruthenium ($Ru^{2+}$), zinc ($Zn^{2+}$) or silver ($Ag^{2+}$) and a free base porphyrin (with $2H^+$ instead of a metal) (see, for example, Patent Literature 3).

There have also been disclosed a method and a device for sensing harmful gases such as halogen gases and hydrogen halide gases by using, as a sensing member, a polymer matrix utilizing a free base porphyrin containing no central metal atom or a zinc tetraphenylporphyrin containing zinc (Zn) as a central metal (see, for example, Patent Literature 4).

CITATION LIST

Patent Literature

Patent Literature 1: WO02/057738A2
Patent Literature 2: National Publication of International Patent Application No. 05-505871
Patent Literature 3: U.S. Pat. No. 6,495,102
Patent Literature 4: U.S. Pat. No. 6,096,557

Non Patent Literature

Non Patent Literature 1: CHEMISTRY LETTERS, pp. 521 to 524, 1988, "Optical Detection of Nitrogen Monoxide by Metal Porphine Dispersed in Amorphous Silica Film," Hiromichi ARAI et al.
Non Patent Literature 2: Journal of the Chemical Society of Japan, 1998, No. 5, pp. 338 to 345, "Nitrogen Monoxide Adsorption and Contact Decomposition Properties of Co(II) Complexes," Makoto MIYAMOTO and Yoshio HANAZATO.

SUMMARY OF INVENTION

Technical Problem

However, according to the conventional constitution, when NO is sensed in the air, the measurement needs to be performed in a vacuum chamber. The gases such as $O_2$ and CO gases present in the air are immediately bonded to a porphyrin containing cobalt as a central metal (hereinafter, referred to as a cobalt porphyrin) to inhibit the reaction with NO, and hence it is impossible to perform accurate quantitative determination of NO.

Accordingly, the conventional methods have a problem that low concentrations of NO at a ppb level cannot be determined in the air with satisfactory accuracy by using simple and compact devices.

In the case of Non Patent Literature 1 where a cobalt porphyrin is supported on the surface of sol-gel silica, the preparation method is cumbersome, a cobalt porphyrin tends to be aggregated, and low concentrations of NO at a ppb level cannot be determined.

The present invention takes as its object the provision of a nitrogen oxide sensing element capable of determining the concentration of NO with high sensitivity and satisfactory accuracy under the condition that a cobalt porphyrin is not affected by reaction inhibitors such as $O_2$ and CO, even though the involved device is simpler and more compact as compared to conventional devices.

In Patent Literature 2, no reactivity to a NO gas is disclosed; even if a gas sensor is prepared by using a cobalt tetrabenzotriazaporphyrin, the absorbance at an optical wavelength of 618 nm or 680 nm in the optical spectrum used for sensing is small, and hence sensing of NO gas of 100 ppb or less is difficult.

Moreover, in Patent Literature 3, no example of sensing of NO, a nitrogen oxide, is presented.

Further, in Patent Literature 4, the pH dependence of reactivity of a porphyrin is utilized, and thus, it is stated that an acidic gas and an oxidative gas can be sensed; however, no example of sensing of a nitrogen oxide gas of a low concentration of 1 ppm or less is presented.

The present invention takes as another object thereof the provision of a nitrogen oxide sensor being excellent in reproducibility and permitting a plurality of times of measurement.

Solution to Problem

The nitrogen oxide sensing element of the present invention is such that a sensing film is formed on the surface of a substrate, the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal.

Additionally, the nitrogen oxide sensing element of the present invention is such that a carrier including a sensing film formed on the surface thereof is supported on the surface of a substrate, the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal.

Specifically, the nitrogen oxide sensing element of the present invention is such that the number of moles of the porphyrin containing cobalt as a central metal, or the single derivative having a porphyrin skeleton containing cobalt as a central metal or the mixture of the derivatives each having a porphyrin skeleton containing cobalt as a central metal is $1\times10^{-6}$ mol/g to $1\times10^{-3}$ mol/g in relation to the unit weight of the polymer in the sensing film.

Specifically, the nitrogen oxide sensing element of the present invention is such that the number of cobalt atoms per the unit area of the sensing film is $10^{12}/cm^2$ to $10^{16}/cm^2$.

Specifically, the nitrogen oxide sensing element of the present invention is such that the porphyrin containing cobalt as a central metal is a cobalt tetraphenylporphyrin.

Specifically, the nitrogen oxide sensing element of the present invention is such that the cobalt as the central metal of the porphyrin containing cobalt as a central metal, or the single derivative having a porphyrin skeleton containing cobalt as a central metal or each derivative in the mixture of the derivatives each having a porphyrin skeleton containing cobalt as a central metal, is a divalent cobalt ion or in an intermingled manner either a divalent cobalt ion or a trivalent cobalt ion.

Additionally, the nitrogen oxide sensing element of the present invention is such that a sensing film is formed on the surface of a non-sensing-light transmitting substrate, the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal.

Additionally, the nitrogen oxide sensing element of the present invention is such that a sensing film is formed on the surface of a sensing-light transmitting substrate, the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal. Specifically, the sensing-light transmitting substrate is a glass substrate, a quartz substrate, a sapphire substrate, a gallium nitride substrate, a plastic substrate, a sheet of paper, a resin, a woven fabric or a nonwoven fabric.

The nitrogen oxide sensing element of the present invention is such that a sensing film is formed on at least a part of the surface of a substrate serving as a light waveguide through which sensing light passes, in particular formed along the light waveguide, the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal.

The nitrogen oxide concentration determination device of the present invention includes: a nitrogen oxide sensing element in which a sensing film is formed on the surface of a non-sensing-light transmitting substrate, the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal; a temperature controller for allowing the temperature of the nitrogen oxide sensing element to get closer to a target temperature; and a determination section in which the substrate of the nitrogen oxide sensing element is irradiated with sensing light, the light reflected through the sensing film is detected, and the nitrogen oxide concentration of a measurement gas brought into contact with the sensing film is calculated on the basis of a change of the sensing light between before and after the sensing film is brought into contact with the measurement gas.

The nitrogen oxide concentration determination device of the present invention includes: a nitrogen oxide sensing element in which a sensing film is formed on the surface of a sensing-light transmitting substrate, the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal; a temperature controller for allowing the temperature of the nitrogen oxide sensing element to get closer to a target temperature; and a determination section in which light transmitting the sensing film of the nitrogen oxide sensing element is detected, and the nitrogen oxide concentration of a measurement gas brought into contact with the sensing film is calculated on the basis of a change of the sensing light between before and after the sensing film is brought into contact with the measurement gas.

The nitrogen oxide concentration determination device of the present invention includes: a nitrogen oxide sensing element in which a sensing film is formed on at least a part of the surface of a substrate serving as a light waveguide through which sensing light passes, in particular formed along the light waveguide, the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal; a temperature controller for allowing the temperature of the nitrogen oxide sensing element to get closer to a target temperature; and a determination section in which light passing through the substrate of the nitrogen oxide sensing element is detected, and the nitrogen oxide concentration of a measurement gas brought into contact with the sensing film is calculated on the basis of a change of the sensing light between before and after the sensing film is brought into contact with the measurement gas.

The nitrogen oxide concentration determination device of the present invention includes: a nitrogen oxide sensor formed integrally of a nitrogen oxide sensing element and a heater for allowing the temperature of the nitrogen oxide sensing element to get closer to a target temperature, the nitrogen oxide sensing element including a sensing film formed on the surface of a non-sensing-light transmitting substrate, the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal; and a determination section in which the substrate of the nitrogen oxide sensor is irradiated with sensing light, the light reflected through the sensing film is detected, and the nitrogen oxide concentration of a measurement gas brought into contact with the sensing film is calculated on the basis of a change of the sensing light between before and after the sensing film is brought into contact with the measurement gas.

The nitrogen oxide concentration determination device of the present invention includes: a nitrogen oxide sensor formed integrally of a nitrogen oxide sensing element and a heater for allowing the temperature of the nitrogen oxide sensing element to get closer to a target temperature, the nitrogen oxide sensing element including a sensing film formed on the surface of a sensing-light transmitting substrate, the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal; and a determination section in which the substrate of the nitrogen oxide sensor is irradiated with sensing light, the light transmitting the sensing film is detected, and the nitrogen oxide concentration of a measurement gas brought into contact with the sensing film is calculated on the basis of a change of the sensing light between before and after the sensing film is brought into contact with the measurement gas.

The nitrogen oxide concentration determination device of the present invention includes: a nitrogen oxide sensor formed integrally of a nitrogen oxide sensing element and a heater for allowing the temperature of the nitrogen oxide sensing element to get closer to a target temperature, the nitrogen oxide sensing element including a sensing film formed on at least a part of the surface of a substrate serving as a light waveguide through which sensing light passes, in particular formed along the light waveguide, the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal; and a determination section in which light passing through the substrate of the nitrogen oxide sensing element is detected, and the nitrogen oxide concentration of a measurement gas brought into contact with the sensing film is calculated on the basis of a change of the sensing light between before and after the sensing film is brought into contact with the measurement gas.

The method for determining a nitrogen oxide concentration of the present invention is such that: a nitrogen oxide sensing element including a sensing film formed on the surface of a non-sensing-light transmitting substrate is used, the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal; and the substrate of the nitrogen oxide sensing element is irradiated with sensing light, the light reflected through the sensing film is detected, and the nitrogen oxide concentration of a measurement gas brought into contact with the sensing film is calculated on the basis of a change of the sensing light between before and after the sensing film is brought into contact with the measurement gas; and heat treatment of the nitrogen oxide sensing element is performed in the determination of the nitrogen oxide concentration. Specifically, the heat treatment is such that: before the measurement gas is brought into contact with a nitrogen oxide sensor, the temperature of the nitrogen oxide sensor is maintained at a first temperature T1 lower than the limit temperature of the nitrogen oxide sensor, then the nitrogen oxide sensor is irradiated with the sensing light under the condition of a second temperature T2 lower than the first temperature T1, and the reflected light through the sensing film is detected as a light output V1; the measurement gas is brought into contact with the nitrogen oxide sensor under the condition of the second temperature T2 and at the same time the nitrogen oxide sensor is irradiated with the sensing light, and the light reflected through the sensing film is detected as a light output V2; and on the basis of the light output V1 and the light output V2, the nitrogen oxide concentration of the measurement gas brought into contact with the nitrogen oxide sensor is calculated. Specifically, the sensing film is composed of a polyethylene oxide (PEO) polymer including as dispersed therein CoTPP containing cobalt as a central metal, and in this case, the limit temperature is 290° C. Additionally, the first temperature T1 is equal to or higher than the melting point of the polymer constituting the sensing film, and the second temperature T2 is equal to or higher than the glass transition point of the polymer constituting the sensing film.

The method for determining a nitrogen oxide concentration of the present invention is such that: a nitrogen oxide sensing element including a sensing film formed on the surface of a sensing-light transmitting substrate is used, the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal; and light transmitting the sensing film of the nitrogen oxide sensing element is detected, and the nitrogen oxide concentration of a measurement gas brought into contact with the sensing film is calculated on the basis of a change of the sensing light between before and after the sensing film is brought into contact with the measurement gas; and heat treatment of the nitrogen oxide sensing element is performed in the determination of the nitrogen oxide concentration. Specifically, the heat treatment is such that: before the measurement gas is brought into contact with a nitrogen oxide sensor, the temperature of the nitrogen oxide sensor is maintained at a first temperature T1 lower than the limit temperature of the nitrogen oxide sensor, then the nitrogen oxide sensor is irradiated with the sensing light under the condition of a second temperature T2 lower than the first temperature T1, and the light transmitting the sensing film is detected as a light output V1; the measurement gas is brought into contact with the nitrogen oxide sensor under the condition of the second temperature T2 and at the same time the nitrogen oxide sensor is irradiated with the sensing light, and the light transmitting the sensing film is detected as a light output V2; and on the basis of the light output V1 and the light output V2, the nitrogen oxide concentration of the measurement gas brought into contact with the nitrogen oxide sensor is calculated. Specifically, the sensing film is composed of a polyethylene oxide (PEO) polymer including as dispersed therein CoTPP containing cobalt as a central metal, and in this case, the limit temperature is 290° C. Additionally, the first temperature T1 is equal to or higher than the melting point of the polymer constituting the sensing film, and the second temperature T2 is equal to or higher than the glass transition point of the polymer constituting the sensing film.

The method for determining a nitrogen oxide concentration of the present invention is such that: a nitrogen oxide sensing element including a sensing film formed on at least a part of the surface of a substrate serving as a light waveguide through which sensing light passes, in particular formed along the light waveguide, is used, the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal; and light transmitting the substrate of the nitrogen oxide sensing element is detected, and the nitrogen oxide concentration of a measurement gas brought into contact with the sensing film is calculated on the basis of a change of the sensing light between before and after the sensing film is brought into contact with the measurement gas; and heat treatment of the nitrogen oxide sensing element is performed in the determination of the nitrogen oxide concentration. Specifically, the heat treatment is such that: before the measurement gas is brought into contact with a nitrogen oxide sensor, the temperature of the nitrogen oxide sensor is maintained at a first temperature T1 lower than the limit temperature of the nitrogen oxide sensor, then the substrate is irradiated with the sensing light under the condition of a second temperature T2 lower than the first temperature T1, and the light transmitting the substrate is detected as a light output V1; and the measurement gas is brought into contact with the nitrogen oxide sensor under the condition of the second temperature T2 and at the same time the substrate is irradiated with the sensing light, the light transmitting the substrate is detected as a light output V2, and on the basis of the light output V1 and the light output V2, the nitrogen oxide concentration of the measurement gas brought into contact with the nitrogen oxide sensor is calculated. Specifically, the sensing film is composed of a polyethylene oxide (PEO) polymer including as dispersed therein CoTPP containing cobalt as a central metal, and in this case, the limit temperature is 290° C. Additionally, the first temperature T1 is equal to or higher than the melting point of the polymer constituting the sensing film, and the second temperature T2 is equal to or higher than the glass transition point of the polymer constituting the sensing film.

Additionally, the optical wavelength of the sensing light is an optical wavelength including the Soret band of the optical absorption band of the porphyrin.

Advantageous Effects of Invention

According to the nitrogen oxide sensing element of the present invention, the concentration of nitrogen oxide can be determined with satisfactory accuracy by a simple and compact device, even in the air, in such a way that the cobalt porphyrin is not affected by reaction inhibitors such as $O_2$ and CO.

Additionally, according to the nitrogen oxide sensor of the present invention, the concentration of nitrogen oxide can be determined with satisfactory accuracy even by a compact device, by performing low-temperature heating in such a way that the cobalt porphyrin is not affected by reaction inhibitors such as $O_2$ and CO. Moreover, it is possible to perform a plurality of times of measurement with satisfactory reproducibility.

DESCRIPTION OF EMBODIMENTS

Hereinafter, the individual embodiments of the present invention are described on the basis of the accompanying drawings.

Embodiment 1

Figure 1:
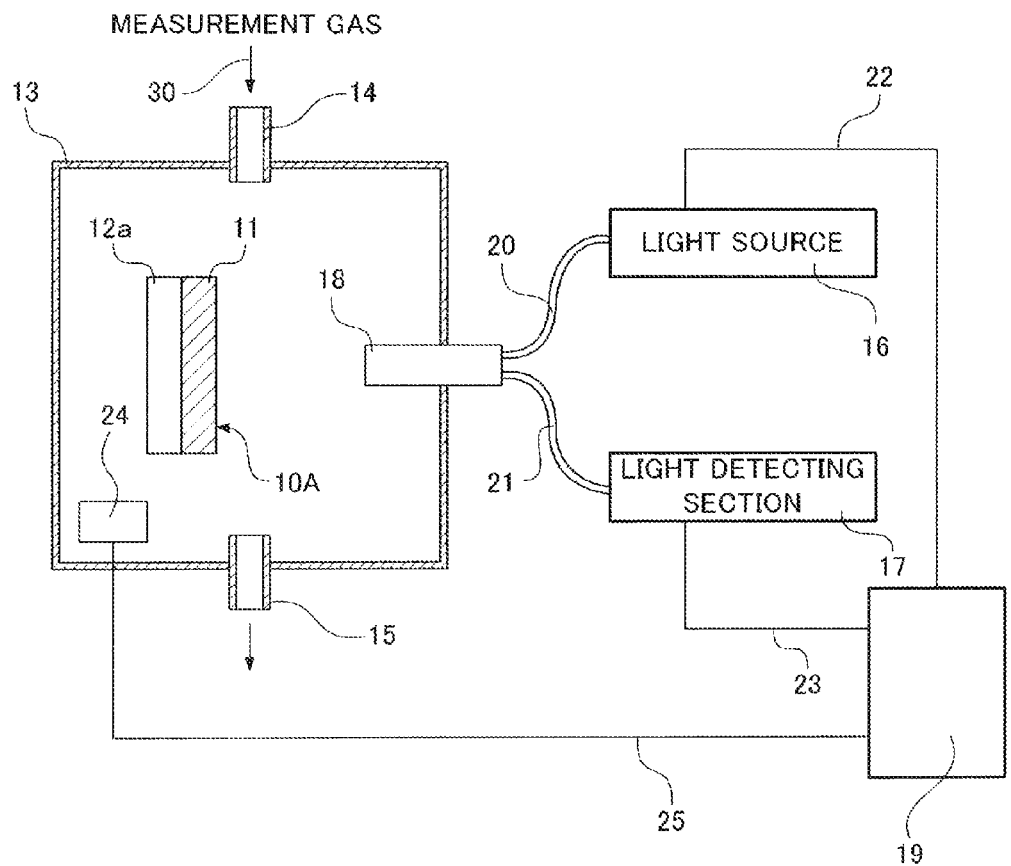
FIG. 1 is a block diagram illustrating a nitrogen oxide concentration determination device using a light reflection measurement sensor in Embodiment 1 of the present invention.

FIG. 1 illustrates a light reflection-type nitrogen oxide concentration determination device using a nitrogen oxide sensing element 10A of the present invention.

The nitrogen oxide sensing element 10A is constituted by a sensing film 11, composed of a polyethylene oxide (PEO) polymer including as dispersed therein CoTPP containing Co as a central metal, and an opaque substrate 12a such as an alumina substrate. The substrate 12a may be made of any material as long as the material can reflect light; preferably, in addition to the alumina substrate, any of the following substrates or a composite of two or more of the following substrates can be adopted as the substrate 12a: a silicon substrate, a silicon carbide substrate, a gallium arsenide substrate, a ceramic substrate, a plastic substrate and a metal plate.

The nitrogen oxide sensing element 10A is set in a measurement cell 13. A measurement gas 30 containing nitrogen oxide is introduced from a gas inlet 14 into the interior of the measurement cell 13 and discharged from a gas outlet 15, and thus the sensing film 11 is exposed to the measurement gas 30.

For the purpose of detecting an optical property change of the sensing film 11 between before and after the sensing film 11 is exposed to the measurement gas 30, in the light reflection-type nitrogen oxide concentration determination device, a light projecting and receiving section 18 is assembled so as to face the nitrogen oxide sensing element 10A. More specifically, the light projecting and receiving section 18 perpendicularly irradiates the sensing film 11 of the nitrogen oxide sensing element 10A with light from a light source 16 through an optical fiber 20, and the reflected light passes through the light projecting and receiving section 18 and an optical fiber 21 and is then detected by a light detecting section 17.

The light detecting section 17 is constituted by an optical band pass filter (not shown), a silicon photodiode (not shown), a photocurrent-voltage conversion circuit (not shown) and an amplification circuit (not shown). The reflected light is converted into an optical detection signal corresponding to the reflected light intensity for measurement.

The measurement cell 13 is equipped with a temperature controller 24, and the control of the temperature inside the measurement cell 13 can be performed with the temperature controller 24. The temperature controller 24 is constituted by a heater, a thermocouple for use in temperature detection and the like (not shown). The light source 16, the light detecting section 17 and the temperature controller 24 are connected to a measurement controller 19 through control wires 22, 23 and 25, respectively, for the purpose of controlling the respective operations of the light source 16, light detecting section 17 and temperature controller 24.

The nitrogen oxide sensing element 10A is fabricated as follows.

The sensing film 11 is formed by dispersing CoTPP, which is a porphyrin containing cobalt as a central metal, in a polyethylene oxide (PEO) polymer (glass transition temperature Tg=−53° C., refractive index n=1.46). The refractive index (hereinafter referred to as n) of the polymer in an optical wavelength range of 380 nm to 800 nm is preferably 1.4 to 1.7. This is because when n is 1.4 to 1.7, the absorbance magnitude is small to be almost transparent and have a transmittance of 90% or more for the optical wavelength used for nitrogen oxide sensing. The use of such a polymer leads to the below-mentioned absorbance change due to a reaction between a porphyrin containing cobalt as a central metal and nitrogen oxide, and hence makes it possible to effectively measure a change of the reflected light or the transmitted light.

Additionally, the glass transition temperature (hereinafter referred to as Tg) of the polymer is preferably −150° C. to 150° C. The use of the polymer in such a glass transition temperature range makes it possible to improve the gas permeability and the response to a nitrogen oxide gas. When Tg is lower than −150° C., the polymer takes a molten state at normal temperature, and the measurement variation at the time of sensing nitrogen oxide is increased. When a polymer having Tg exceeding 150° C. is used, heat treatment at a temperature of 250° C. or higher is required for the purpose of attaining high sensitivity to nitrogen oxide, leading to degradation of CoTPP. Details of effects on the Tg of the polymer and the nitrogen oxide sensing element are described later.

The principle of a NO sensing method with the nitrogen oxide sensing element 10A is described.

Figure 2:
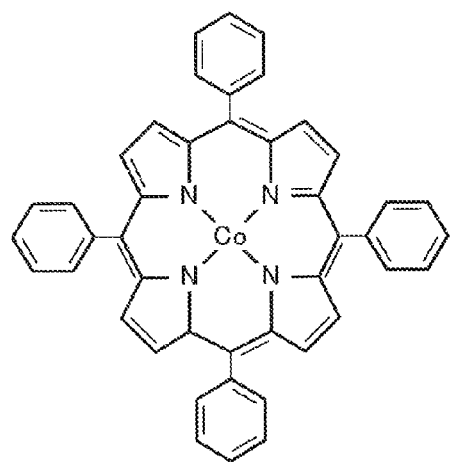
FIG. 2 illustrates the structure of CoTPP used in a nitrogen oxide sensing element in the same embodiment.

The structure of CoTPP serving as a NO sensing agent is shown in FIG. 2.

Figure 3:
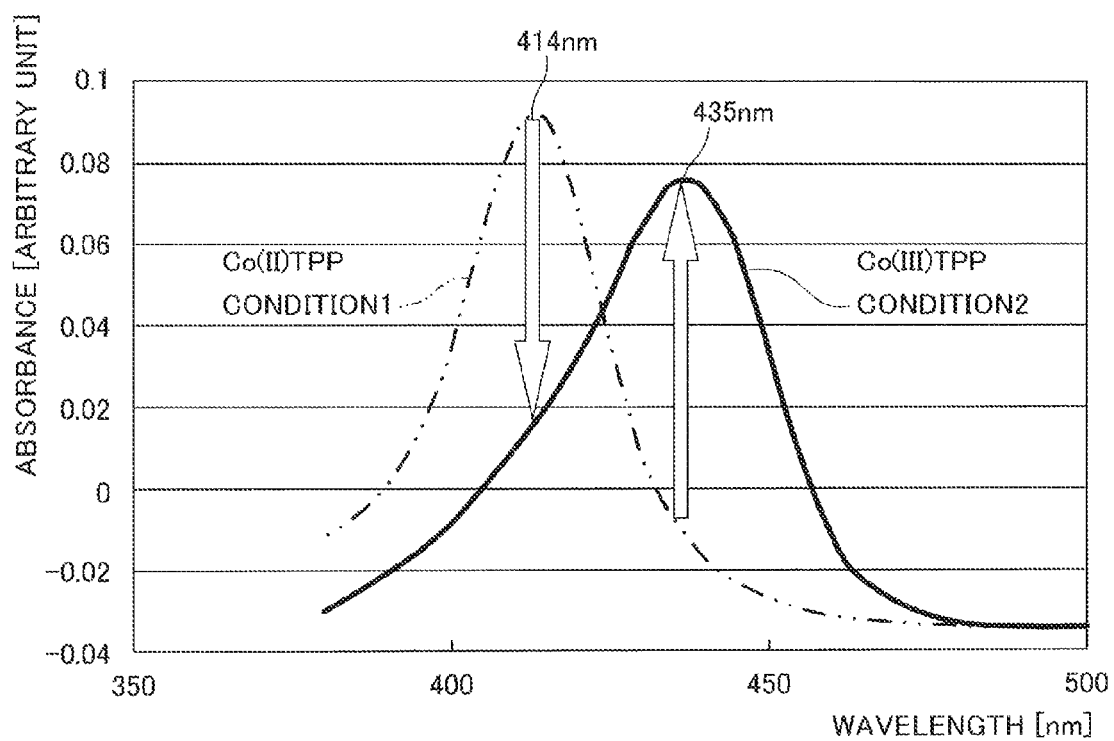
FIG. 3 shows the optical absorption spectra of the nitrogen oxide sensing element in the same embodiment.

CoTPP is a porphyrin containing cobalt as a central metal, and has four phenyl groups on the periphery of the porphyrin skeleton. When NO is bonded to CoTPP containing divalent cobalt as a central metal, an electron is transferred from the cobalt to the NO, and the cobalt is oxidized to trivalent cobalt. Consequently, the absorption band due to CoTPP containing divalent cobalt (hereinafter referred to as Co(II)TPP), having a central wavelength of 414 nm, is attenuated as shown in FIG. 3, and newly there grows an absorption band due to CoTPP containing trivalent cobalt (hereinafter referred to as Co(III)TPP), having a central wavelength of 435 nm.

The change magnitudes of these absorption bands depend on the NO concentration, and hence the NO concentration can be determined from the change magnitudes of the CoTPP absorption bands caused by exposure to NO. The changes of the absorption bands can be determined by measuring the reflection spectra of the sensing film before and after the exposure to NO. Accordingly, the NO concentration can be determined by using CoTPP. CoTPP containing divalent cobalt having reactivity to NO has only to be present in the sensing film; and CoTPP containing in an intermingled manner either divalent cobalt or trivalent cobalt may also be adopted. When such an intermingled condition is involved, there develops, in the absorption spectrum of FIG. 3, a superposed absorption band composed of the 414-nm absorption band due to CoTPP containing divalent cobalt and the 435-nm absorption band due to CoTPP containing trivalent cobalt. The ratio between CoTPP containing divalent cobalt and CoTPP containing trivalent cobalt is determined by the concentration of the CoTPP dispersed in the polymer of the sensing film and the NO sensitivity of the system, and is not limited.

However, the nitrogen oxide sensing element 10A fabricated by the above-described method reacts with $O_2$ or CO in the air, Co(III)TPP containing trivalent cobalt becomes the main component, and if this situation is maintained, it is impossible to measure the bonding amount of NO with satisfactory accuracy. This is because when sensing of NO is performed by using Co(III)TPP containing trivalent cobalt as a central metal, $O_2$ or CO, a reaction inhibitor, is bonded to the cobalt, and hence the reaction efficiency with NO is decreased.

Accordingly, for the purpose of determining the NO concentration with satisfactory accuracy, pretreatment to change CoTPP to CoTPP containing divalent cobalt is required immediately before the measurement of a nitrogen oxide gas. As the pretreatment method, irradiation of the sensing film 11 with light or irradiation of the sensing film 11 with electromagnetic wave such as microwave, or a combination of these may be adopted. In consideration of simplicity of the nitrogen oxide sensing and size reduction of the measurement device, heat treatment is preferable.

Here, the heat treatment is described.

Figure 4:
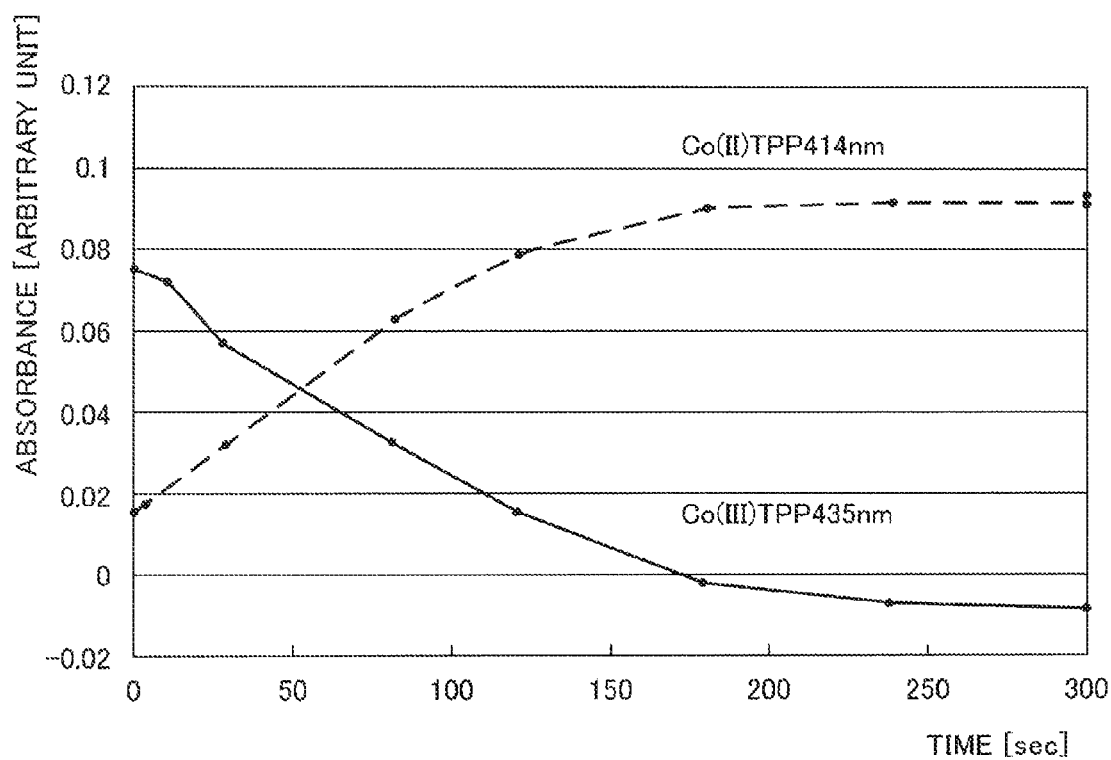
FIG. 4 shows the relations between absorbances at 414 nm and 435 nm of the nitrogen oxide sensing element and a heating time when the nitrogen oxide sensing element was heated at 150° C. in the same embodiment.

When CoTPP is heated, the molecule of a gas such as $O_2$ and CO bonded to CoTPP is detached and the cobalt of CoTPP is reduced to divalent cobalt. FIG. 4 shows the 414-nm absorbance change and the 435-nm absorbance change of CoTPP when the nitrogen oxide sensing element 10A was heated at 150° C. At the time of heating, an inert gas such as $N_2$ gas and Ar gas, or air may be made to flow. By making such a gas flow, it is possible to effectively remove the detached molecules of the gas such as $O_2$ gas and CO gas from the measurement cell.

At the start of heating at 150° C., the absorbance of the peak of the absorption band due to Co(III)TPP having a central wavelength of 435 nm is decreased, and at the same time, the absorbance of the peak of the absorption band due to Co(II)TPP having a central wavelength of 414 nm is increased. In about three minutes from the start of heating, the absorbances at both of these wavelengths are saturated, and the absorption band of Co(II)TPP having a peak at the central wavelength of 414 nm shown in FIG. 3 is obtained.

As described above, the nitrogen oxide sensing element 10A of the present embodiment can reduce CoTPP so as to have divalent cobalt with heat treatment for an extremely short period of time, and thus can be used for NO determination.

When the heating temperature is decreased to 50° C. in the heat treatment, the time taken for changing CoTPP so as to have divalent cobalt is extended; however, after a predetermined time has elapsed, the nitrogen oxide sensing element 10A having the sensing film 11 exhibiting the absorption band of FIG. 3 is obtained. On the other hand, when the heating temperature is set at 250° C., the absorbance is decreased over the whole involved wavelength range probably because of the degradation of CoTPP or the PEO polymer.

Therefore, the setting of the heating temperature and the heating time is not specifically limited to the above-described heating temperature and heating time as long as CoTPP and the PEO polymer are not degraded and the heat treatment can be performed rapidly; however, the temperature range in the heat treatment is preferably from 50° C. to 200° C.

As a factor permitting the reduction of CoTPP so as to have divalent cobalt with heat treatment in a short period of time, the effect due to PEO contained in the sensing film, 11 is considered. The involved mechanism is described with reference to the conceptual diagram of the sensing film 11.

Figure 5:
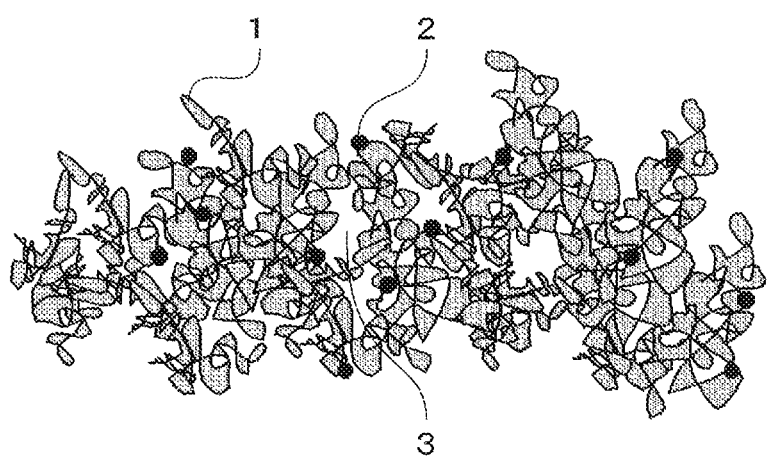
FIG. 5 is an enlarged conceptual diagram of a sensing film in the same embodiment.

FIG. 5 shows an enlarged conceptual diagram of a part of the sensing film 11.

In FIG. 5, reference numeral 1 denotes PEO and reference numeral 2 denotes CoTPP. The glass transition temperature of PEO 1 is as low as −53° C.; hence, at normal temperature, a free space 3 which is a space not occupied by atoms (or molecules) is large, PEO 1 is in a glassy state, a part of amorphous molecules undergo free vibration, and hence the gas permeability of the sensing film 11 is extremely satisfactory.

Therefore, the diffusion time due to gas diffusion, offering a problem in a common solid, can be neglected as compared to the redox time of CoTPP. Because of the above-described satisfactory gas permeability, when Co(III)TPP is reduced, the reaction inhibitor adsorbed on CoTPP 2 can be efficiently detached.

Further, PEO 1 has an effect of preventing the aggregation of CoTPP 2. When PEO 1 is not contained, almost all the CoTPP 2 molecules mutually aggregate, and the reactivity of CoTPP to NO is remarkably degraded.

The polymer is not limited to PEO, and has only to be a polymer which is transparent for the measurement optical wavelengths as described above, has a low glass transition temperature and prevents the aggregation of CoTPP. The lower limit of the glass transition temperature Tg is preferably as low as possible from the viewpoint that the power consumption of the nitrogen oxide concentration determination device is suppressed to low power; however, the polymer is preferably solid at normal temperature, and specifically the lower limit of the glass transition temperature Tg is $-150°$ C. or higher. The upper limit of Tg is preferably such that the polymer has CoTPP, the properties of which are not affected by the heat treatment temperature, and thus, the upper limit of Tg is set at 150° C.

Accordingly, examples of polymers satisfying the above-described conditions, other than PEO (n=1.46, Tg=$-53°$ C., Tm=68° C.) may include: acrylic resins such as polyisobutyl methacrylate (n=1.42, Tg=48° C., Tm=140° C.) polymethyl acrylate (n=1.49, Tg=66° C.) and polyacrylonitrile (n=1.52, Tg=97° C.); vinyl resins such as polystyrene (n=1.59, Tg=100° C.), polyvinyl chloride (n=1.63, Tg=81° C.) and polyvinyl alcohol (n=1.49, Tg=85° C.); polydimethylsiloxane (n=1.42, Tg=$-123°$ C.); ethyl cellulose (n=1.47, Tg=43° C., Tm=200° C.); and biodegradable plastics such as polycaprolactan (n=1.40, Tg=$-62°$ C., Tm=60.1° C.), polybutylene succinate (n=1.68, Tg=$-33°$ C., Tm=112° C.) and polybutylene succinate adipate (n=1.70, Tg=$-42°$ C., Tm=96.7° C.).

These resins include copolymers for copolymerizable resins and modified resins for resins modifiable with side chain substituents for the purpose of improving the refractive index or the heat resistance.

Additionally, for the purpose of improving the fluidity, the above-described polymers may include plasticizers. For example, even ethyl cellulose (n=1.47, Tg=43° C., Tm=200° C.) in which dioctyl phthalate, a plasticizer for use in polymer, is mixed can substitute for PEO. By mixing a plasticizer in a polymer, the fluidity of the polymer is improved, so that the melting point Tm is effectively decreased, the gas diffusion rate is improved and the reaction with the gas is allowed to proceed more rapidly.

Next, the stability of the CoTPP dispersed in the polymer after heat treatment is described.

The reactivity between CoTPP and an analyte gas is determined by the relationship between the electronic states of CoTPP and the analyte gas. Specifically, the reactivity is determined by the magnitude of a redox potential difference determined by the electronic states of CoTPP and the analyte gas, and a change of the optical absorption band of CoTPP occurs depending on the redox reaction. Because the present inventors have discovered that the reactivities of CoTPP to other gases as compared to the reactivity of CoTPP to the nitrogen oxide gas NOx such as NO or $NO_2$ are extremely low, it is inferred that a redox potential difference between CoTPP and NOx is smaller as compared to redox potential differences between CoTPP and other gases, and thus the reactivity between CoTPP and NOx is high. The present inventors have verified that after heat treatment, the reactivity to $O_2$ or CO, a reaction inhibitor, is extremely lower as compared with the reactivity to NOx, and hence, the divalent state of CoTPP can be maintained in the sensing film of the present invention within at least 10 minutes under the condition not being exposed to the NOx gas. Therefore, owing to the pretreatment, by exposing CoTPP containing divalent cobalt to the nitrogen oxide gas, the nitrogen oxide gas can be extremely effectively sensed.

The NO sensing agent is not limited to CoTPP, and has only to be any of a porphyrin containing cobalt as a central metal and undergoing a change of the absorption band thereof due to bonding of NO thereto, a single derivative having a porphyrin skeleton containing cobalt as a central metal and undergoing a change of the absorption band thereof due to bonding of NO thereto, and a mixture of derivatives each having a porphyrin skeleton containing cobalt as a central metal and undergoing a change of the absorption band thereof due to bonding of NO thereto. The same effect can be obtained, for example, even by using any of the following compounds as these porphyrin derivatives each having cobalt as a central metal: 2,3,7,8,12,13,17,18-octaethyl-21H,23H-porphine cobalt, 5,10,15,20-tetrakis(4-methoxyphenyl)-21H,23H-porphine cobalt (hereinafter referred to as Co(p-$OCH_3$)TPP), 2,8,12,18-tetraethyl-3,7,13,17-tetramethyl-21H,23H-porphine cobalt, 5,10,15,20-tetrakis(4-sulfonatophenyl)-21H,23H-porphine cobalt, or 5,10,15,20-tetrakis(4-hydroxyphenyl)-21H,23H-porphine cobalt (hereinafter referred to as CoTP(CoTP(OH)$_4$P)).

The CoTPP dispersed in the polymer of the sensing film 11 undergoes, as described above, changes in the absorption spectrum thereof when exposed to the nitrogen oxide gas, and hence, by measuring the reflectivity of the sensing film 11 before and after the exposure to the gas, the nitrogen oxide concentration in the measurement gas can be derived.

A method for fabricating the nitrogen oxide sensing element 10A is described more specifically.

First, CoTPP and PEO are added in chloroform to prepare a solution and the solution is stirred to prepare a CoTPP-PEO solution having a CoTPP concentration of $1 \times 10^{-4}$ mol/L and a PEO concentration of 1 (wt/vol) %. Next, the CoTPP-PEO solution is applied onto a 1-cm square alumina substrate 12a by spin coating and dried to prepare the sensing film 11. The thickness of the sensing film 11 measured with a film thickness meter is about 0.5 μm. By the above-described method, the nitrogen oxide sensing element 10A is fabricated.

The thickness of the sensing film 11 is set according to the reactivity of the sensing film to the nitrogen oxide gas. When the CoTPP concentration is constant, the sensitivity is increased with an increase in the film thickness, but the response to the nitrogen oxide gas is made slow. When the thickness of the sensing film is thin, the sensing film is degraded with an increasing number of times of use. Accordingly, in consideration of the sensing limit of the nitrogen oxide gas, the response to the nitrogen oxide gas, and the durability, the thickness of the sensing film 11 is preferably 0.1 μm to 3 μm.

In the above-described constitution, details of the practical procedure of the concentration sensing of a nitrogen oxide gas are as follows.

First, for the purpose of determining the NO concentration with satisfactory accuracy, heat treatment for changing CoTPP to CoTPP containing divalent cobalt is performed by using the temperature controller 24. The heat treatment conditions are, for example, such that the heating temperature is 150° C., a flow of nitrogen gas (flow rate: 200 ml/min) is used and the heating time is 10 minutes.

Next, the temperature of the nitrogen oxide sensing element is set at 100° C. with the temperature controller 24, and then, NO, the measurement gas, is introduced from the gas inlet 14 into the measurement cell 13. When NO is adsorbed to the CoTPP of the sensing film 11, an electron is transferred from the cobalt of the CoTPP to NO to oxidize the CoTPP, and consequently, in the optical reflection spectrum, the absorption band at the wavelength of 414 nm is decreased in intensity, so that the optical reflectivity at the wavelength of 414 nm is increased. At the same time the absorption band at the wavelength of 435 nm is increased in intensity, and consequently the optical reflectivity at the wavelength of 435 nm is decreased.

In the light detecting section 17, by means of an optical band pass filter (not shown) meeting the above-described change of the optical absorption band, a silicon photodiode (not shown), a photocurrent-voltage conversion circuit (not shown) and an amplification circuit (not shown), the reflected light is converted into an optical detection signal corresponding to the nitrogen oxide concentration to be determined.

Figure 6:
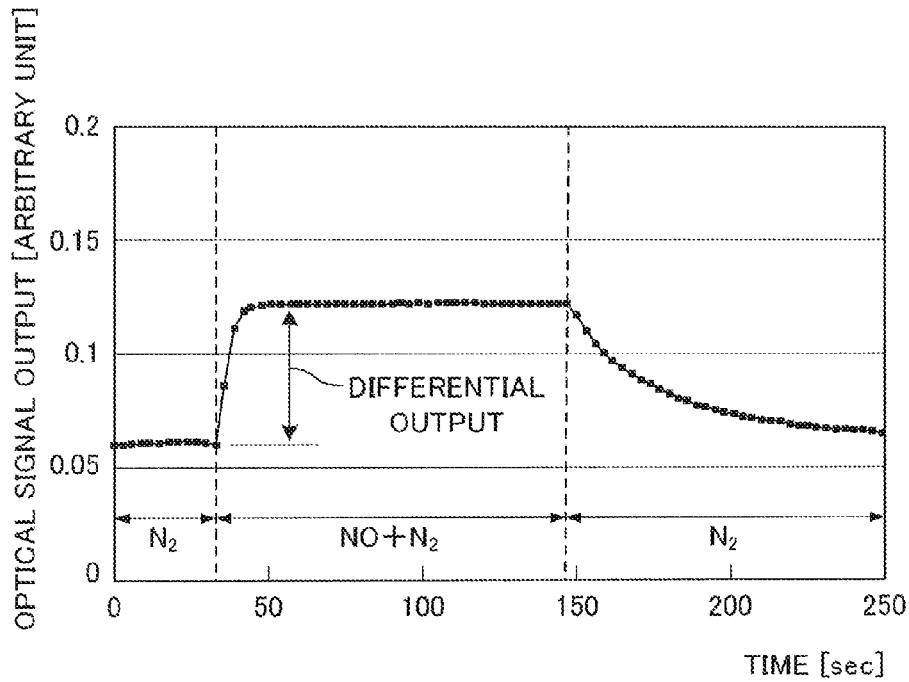
FIG. 6 is an explanatory graph of the optical signal output of a NO gas when NO of 1 ppm was sensed by the nitrogen oxide concentration determination device using the light reflection measurement sensor in the same embodiment.

FIG. 6 shows a time change of the optical signal output observed when the light reflection measurement sensor 10A was alternately exposed with a period of 2 minutes to a NO gas (base: nitrogen, concentration: 1 ppm, flow rate: 200 ml/min) and a nitrogen gas (flow rate: 200 ml/min).

From FIG. 6, it is seen that the absorption spectrum of the CoTPP in the sensing film is changed largely when the sensing film is exposed to the NO gas, the corresponding optical signal output is changed and the sensor response reaches a stationary value in a time as extremely short as about 10 seconds.

Figure 7:
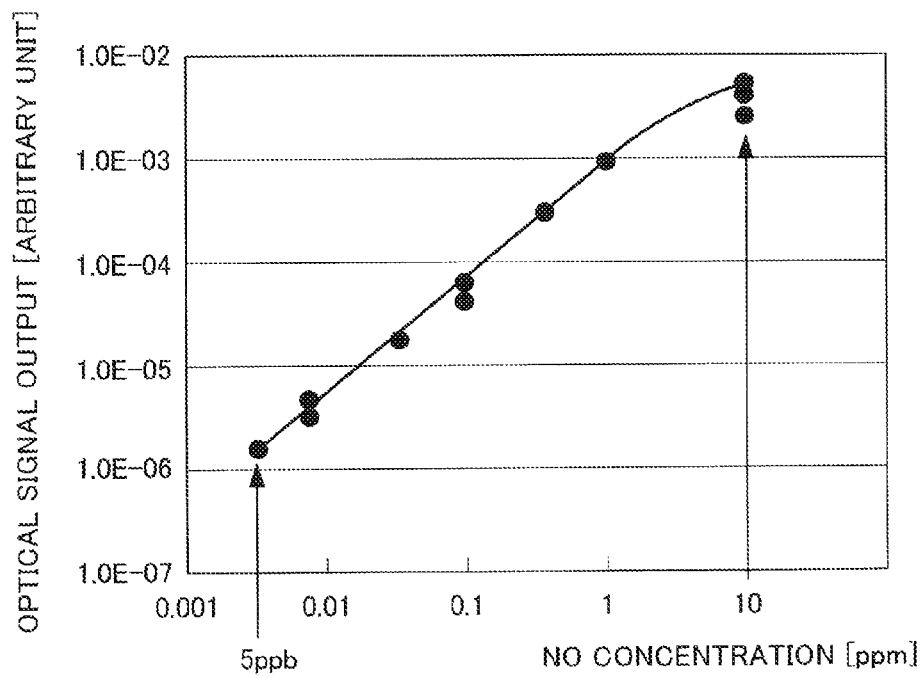
FIG. 7 shows the relation between the NO concentration and the optical signal output, measured by using a nitrogen oxide sensor in the same embodiment.

By using the above-described procedure, the optical signal output was measured while the nitrogen oxide concentration, namely, the NO gas concentration was being changed from 5 ppb to 10 ppm. FIG. 7 shows the relation between the NO concentration and the optical signal output measured with the nitrogen oxide sensing element 10A of the present invention. From FIG. 7, it is seen that by using the nitrogen oxide sensing element of the present invention, the NO concentration can be determined in the NO concentration range from 5 ppb to 10 ppm.

As the pretreatment of the nitrogen oxide sensing element, heat treatment is performed at a first predetermined temperature of 150° C., with a flow of nitrogen gas (flow rate: 200 ml/min) for 10 minutes, and thus the CoTPP dispersed in the polymer is initialized to CoTPP containing divalent cobalt as a central metal; successively, the temperature controller 24 is operated for the interior of the measurement cell 13 to be set at a second predetermined temperature of 70° C., then the sensing film 11 is irradiated with light having a central wavelength of 430 nm from the light source 16, a first optical signal output V(5 ppb)01 from the initialized sensing film is measured and the measured value is stored in the measurement controller 19.

The NO gas (base: nitrogen, concentration: 5 ppb, flow rate: 200 ml/min) is made to flow toward the sensing film 11 for 10 seconds, and the optical signal output at the elapsed time of 10 seconds is measured to obtain a second optical signal output V(5 ppb)11. In the measurement controller 19, the measurement results are stored as the following differential output:

differential output $\Delta V(5\ ppb)1 = V(5\ ppb)11 - V(5\ ppb)01$

With the same gas concentration, a set of the initialization, the exposure to the NO gas and the measurement is repeated five times to obtain five measurement values, $\Delta V(5\ ppb)1$ to $\Delta V(5\ ppb)5$.

Under the same conditions except for the NO gas concentration, the optical signal output is measured at each of the following NO gas concentrations: 10 ppb, 50 ppb, 100 ppb, 500 ppb and 1 ppm; thus a calibration curve between the NO gas concentration and the optical signal output is obtained and stored in the measurement controller 19.

The change curve of the differential output $\Delta V$ corresponding to the gas concentration is obtained in the measurement controller 19, on the basis of data obtained from measurement with known gas concentrations, and the curve thus obtained is established as the characteristic curve of the calibration curve.

The concentration of the analyte gas is determined as follows, with reference to the characteristic curve of the calibration curve stored in the measurement controller 19 as described above or the mathematical expression specifying the characteristic curve of the calibration curve.

Also when the analyte gas undergoes measurement, the NO gas concentration of the analyte gas can be obtained in the same manner as in obtaining the calibration curve. Before the analyte gas undergoes measurement, heat treatment is performed at 150° C. in a flow of nitrogen gas (flow rate: 200 ml/min) for 10 minutes, and thus the CoTPP dispersed in the polymer is initialized to CoTPP containing divalent cobalt as a central metal. Successively, after the sensor temperature is set at the second predetermined temperature of 70° C., then the sensing film is irradiated with LED light (central wavelength: 430 nm) 16, the first optical signal output V(X)01 of the initialized sensing film is measured and the measured value is stored in the measurement controller 19. Successively, the analyte gas (flow rate: 200 ml/min) is made to flow toward the sensing film for 10 seconds, and the optical signal output at the elapsed time of 10 seconds is measured to obtain a second optical signal output V(X)11. In the measurement controller 19, the following differential output at the time of measurement of the analyte gas is calculated from the above-described optical signals:

differential output $\Delta V(X)1 = V(X)11 - V(X)01$, the gas concentration can be read out with reference to the beforehand stored characteristic curve of the calibration curve, or the NO gas concentration of the analyte gas can be calculated by substituting the calculated differential output into the mathematical expression specifying the characteristic curve of the calibration curve.

As described above, according to the measurement method of the present invention, first, heat treatment is performed at the time of measurement, the analyte gas is measured at a predetermined temperature, and by comparing the obtained optical signal output with the value of the beforehand obtained calibration curve between the NO gas concentration and the optical signal output, the NO concentration can be determined with high sensitivity and over a wide concentration range.

In the present embodiment, the heat treatment temperature, the treatment time and the standard gas concentrations used at the time of preparation of the calibration curve are not limited, and the nitrogen oxide concentration can be determined over a range from 5 ppb to 10 ppm by making the CoTPP dispersed in the polymer contain divalent cobalt ion or in an intermingled manner either divalent cobalt ion or trivalent cobalt ion, and by making constant the heat treatment temperature, the treatment time and the gas flow rate condition at the time of preparation of calibration curve.

In the case of the light reflection type nitrogen oxide concentration determination device shown in FIG. 1, a non-light-transmitting opaque substrate is used for the substrate 12a;

however, it is also possible to make a light reflection-type nitrogen oxide concentration determination device, by using the nitrogen oxide sensing element 10A which is fabricated by using a translucent light-transmitting substrate as the substrate, forming on the translucent substrate a film having a surface condition capable of obtaining light reflection, for example, a metal film with a thickness sufficient to block light transmission, and forming the sensing film 11 on the metal film. Also in the case of a metal plate, when the surface condition of the metal plate is capable of obtaining light reflection, it is possible to make a light reflection-type nitrogen oxide concentration determination device by using the nitrogen oxide sensing element 10A fabricated by forming the sensing film 11 on the metal plate.

Further, in the case of the light reflection-type nitrogen oxide concentration determination device shown in FIG. 1, the sensing film 11 is irradiated with light from the light projecting and receiving section 18, and the reflected light can be detected by the light projecting and receiving section 18, and hence there is a feature that the assembling of the optical components is easy.

Embodiment 2

Figure 8:
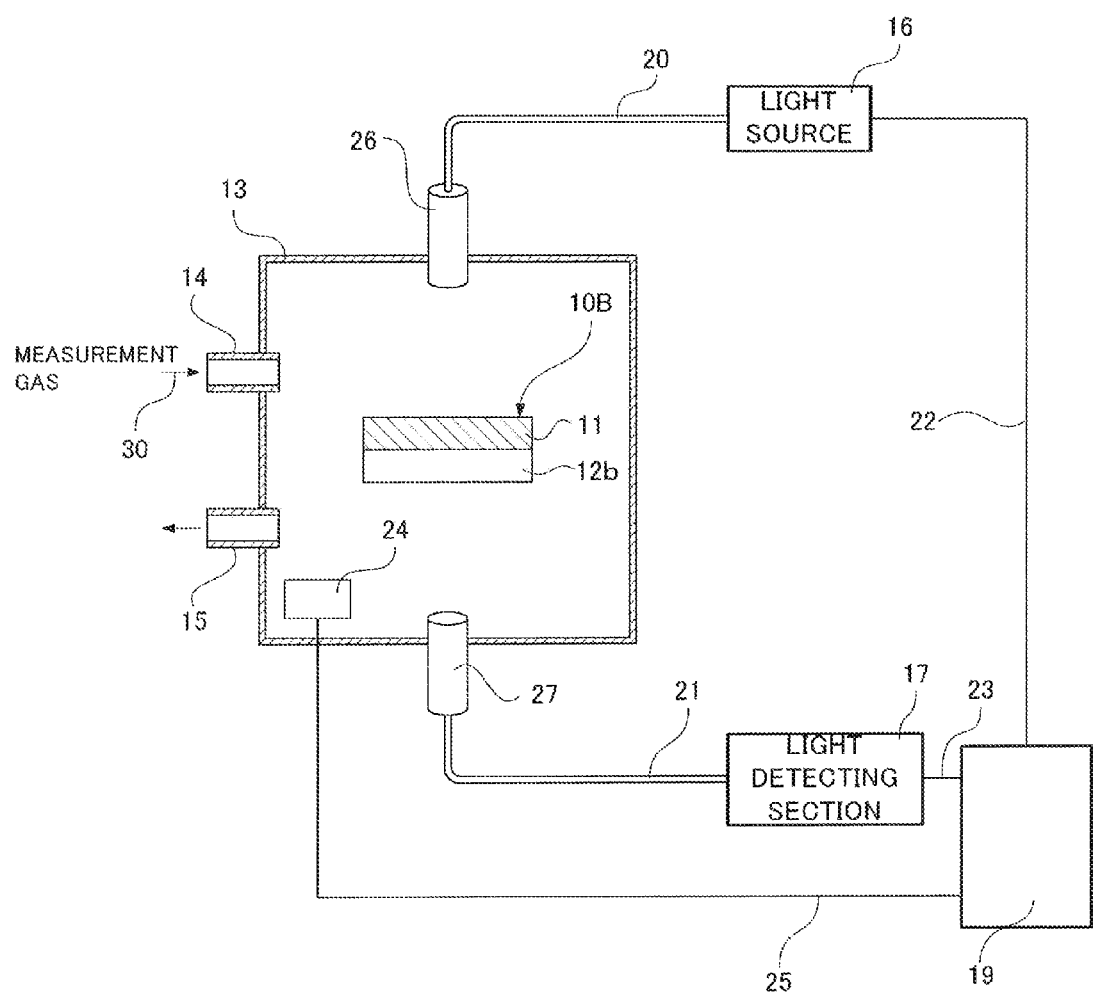
FIG. 8 is a block diagram illustrating a nitrogen oxide concentration determination device using a light transmission-type nitrogen oxide sensing element in Embodiment 2 of the present invention.

FIG. 8 illustrates a light transmission-type nitrogen oxide concentration determination device using a nitrogen oxide sensing element 10B of the present invention.

In the case of the light reflection-type nitrogen oxide concentration determination device of Embodiment 1, used is the nitrogen oxide sensing element 10A fabricated by forming the sensing film 11 on the non-light-transmitting substrate 12a or by forming the sensing film 11 on a film having a surface condition capable of obtaining light reflection, which is formed with a thickness sufficient to block light transmission, on a translucent substrate; however, Embodiment 2 is different from Embodiment 1 in that, in Embodiment 2, sensing light transmits a sensing film 11 and a substrate 12b.

A sufficiently light transmitting material is used for the substrate 12b, and others such as the structure and the fabrication method are the same as in the above-described nitrogen oxide sensing element 10A of Embodiment 1. The material for the substrate 12b is preferably a glass substrate, a quarts substrate, a sapphire substrate, a gallium nitride substrate, a plastic substrate, a sheet of paper, a resin, a woven fabric or a nonwoven fabric. The nitrogen oxide sensing element 10B composed of the sensing film 11 and the translucent substrate, specifically, the transparent substrate 12b is placed inside a measurement cell 13, a measurement gas 30 is introduced from a gas inlet 14 into the measurement cell 13, the sensing film 11 is exposed to the measurement gas 30, and the measurement gas 30 is discharged from a gas outlet 15. In the case of a substrate having no rigidity, namely, a substrate made of paper, resin, woven fabric or nonwoven fabric, it is preferable to use the nitrogen oxide sensing element 10B including the substrate 12b made of paper, resin, woven fabric or nonwoven fabric under the condition that the nitrogen oxide sensing element 10B is supported on a frame (not shown) having an opening in a light transmitting section.

CoTPP in the nitrogen oxide sensing element 10B undergoes a change of the absorption spectrum thereof when exposed to nitrogen oxide, and hence the nitrogen oxide concentration in the measurement gas can be derived by measuring the optical transmittances of the sensing film 11 before and after the exposure of the sensing film 11 to the measurement gas 30.

Light emitted from a light source 16 passes through an optical fiber 20 and a light projecting section 26, and then irradiates the nitrogen oxide sensing element 10B; the light transmitting the nitrogen oxide sensing element 10B passes through a light receiving section 27 and an optical fiber 21, and is then detected by a light detecting section 17. The light detecting section 17 is constituted by an optical band pass filter (not shown), a silicon photodiode (not shown), a photocurrent-voltage conversion circuit (not shown) and an amplification circuit (not shown).

The concerned arrangement is such that the light radiating from the light projecting section 26 is perpendicularly incident on the nitrogen oxide sensing element 10B, and the light transmitting the nitrogen oxide sensing element 10B irradiates the light receiving section 27. The measurement cell 13 is equipped with a temperature controller 24, and the control of the temperature inside the measurement cell 13 can be performed with the temperature controller 24. The temperature controller 24 is constituted by a heater, a thermocouple for use in temperature detection and the like (not shown). The light source 16, the light detecting section 17 and the temperature controller 24 are connected to a measurement controller 19 through control wires 22, 23 and 25, respectively, for the purpose of controlling the respective operations of the light source, light detecting section and temperature controller. The sensing procedure of a nitrogen oxide gas is the same as the procedure in Embodiment 1.

Embodiment 3

Figure 9:
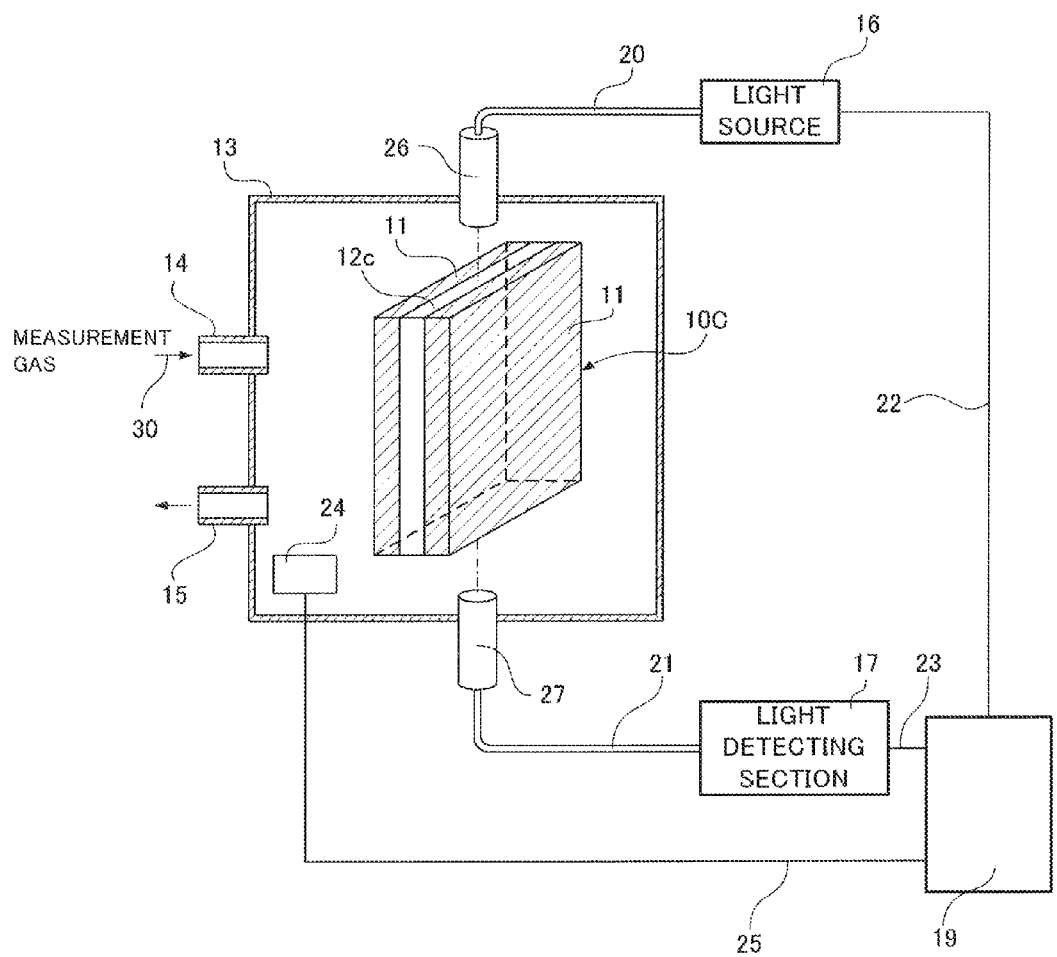
FIG. 9 is a block diagram illustrating a nitrogen oxide concentration determination device using a light waveguide-type nitrogen oxide sensing element in Embodiment 3 of the present invention.

FIG. 9 shows a light waveguide-type nitrogen oxide concentration determination device using a nitrogen oxide sensing element 10C of the present invention.

The nitrogen oxide sensing element 10C is such that sensing films 11, 11 are formed on both sides of a light-transmitting plate-like substrate 12c. The constitution other than the nitrogen oxide sensing element 10C is the same as in Embodiment 2.

The refractive index n0 of the substrate 12c is 1.4 to 1.5, and the refractive index n1 of the sensing films 11, 11 is 1.5 to 1.8. When the lengthwise end face of the nitrogen oxide sensing element 10C is irradiated with diffusion light under such conditions, almost all of the light penetrates from the substrate 12c into the sensing films 11, 11.

In the present embodiment, the end face of the nitrogen oxide sensing element 10C is irradiated with diffusion light, but parallel light can also be used. In the case of parallel light, the end face of the nitrogen oxide sensing element 10C is obliquely irradiated.

Figure 10:
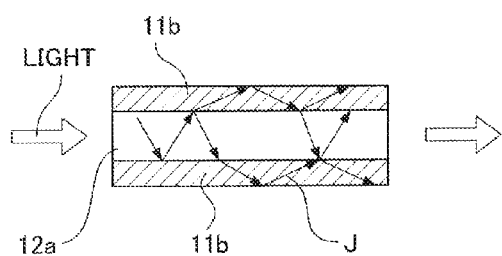
FIG. 10 illustrates the principle of light amplification due to wave guiding in a film in the same embodiment.

As illustrated in a schematic diagram shown in FIG. 10, the light penetrating into the sensing films 11, 11 travels in the sensing films 11, 11, and is reflected on the interfaces between the sensing films 11, 11 and the air, and almost all the reflected light is reflected on the substrate 12c and the sensing films 11, 11. As described above, the light wave-guided into the sensing films propagates in the sensing films 11, 11 as shown by a symbol J, and is wave-guided in the films while undergoing multiple reflection on the interfaces between the sensing films and the air and the interfaces between the sensing films and the substrate. In this way, as a result of the multiple reflection, the optical transmittance can be largely reduced, the sensitivity to NO can be increased and thus optical amplification can be performed.

In FIG. 9, the sensing films 11, 11 are formed on both sides of the substrate 12c, but the sensing film 11 may also be formed on only one side. In such a case, the sensitivity to NO is approximately 50% of the sensitivity in the case of FIG. 9.

A method for fabricating the nitrogen oxide sensing element 10C is described.

First, CoTPP and PEO are added in chloroform to prepare a solution and the solution is stirred to prepare a CoTPP-PEO solution having a CoTPP concentration of $1\times10^{-4}$ mol/L and a PEO concentration of 1 (wt/vol) %. Next, a glass plate (length: 125 mm, width: 2.5 mm, thickness: 0.7 mm, Eagle 2000, manufactured by Corning Inc.) is immersed in the CoTPP-PEO solution for 10 seconds. Then, the substrate is pulled up at an appropriate speed and dried at room temperature. Thus, the nitrogen oxide sensing element 10C in which the sensing films 11, 11 are formed on the plate-like substrate 12c is fabricated.

When the sensing film 11 is formed only on one side of the substrate 12c, only the sensing film 11 on the other side may be peeled off after the above-described fabrication, or when coating by immersing is performed, the immersion may be performed with one side covered with a masking tape.

The procedure of introduction of a measurement gas 30 into a measurement cell 13 and the procedure of the measurement process are the same as in Embodiment 2.

According to the present embodiment, light is repeatedly reflected between the sensing films and the air, the wave guiding in the films is repeated and thus the sensitivity to the NO gas can be increased.

When the end face of the nitrogen oxide sensing element 10C is irradiated with parallel light, the incident angle effective for the multiple reflection of waves guided in the film can be set by using an optical prism.

Embodiment 4

Figure 11:
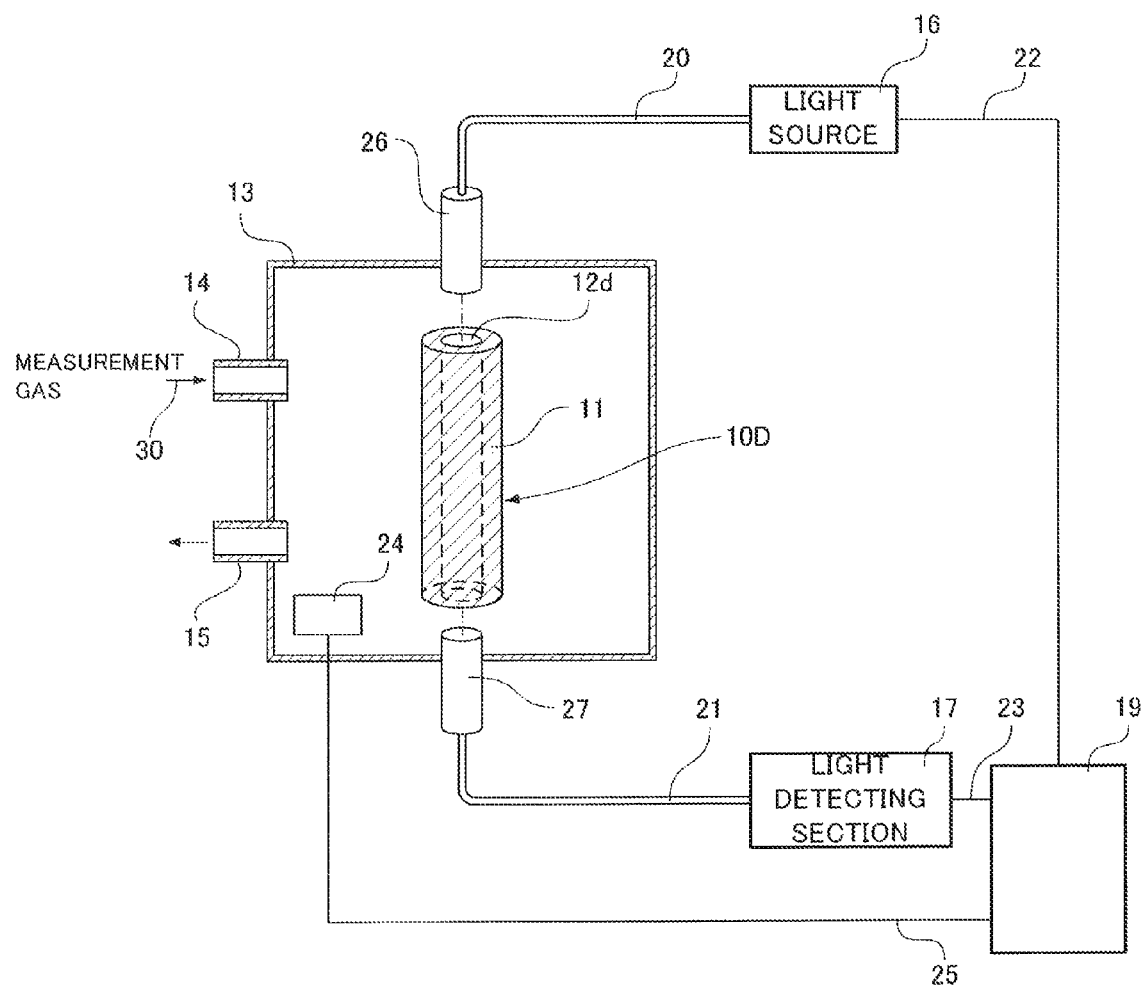
FIG. 11 is a block diagram illustrating a nitrogen oxide concentration determination device using a light waveguide-type nitrogen oxide sensing element in Embodiment 4 of the present invention.

FIG. 11 shows a light waveguide-type nitrogen oxide concentration determination device using a nitrogen oxide sensing element 10D of the present invention.

The nitrogen oxide sensing element 10C is such that the sensing films are formed on both sides of the plate-like substrate 12c or the sensing film is formed on one side thereof; however, the nitrogen oxide sensing element 10D of Embodiment 4 is different from the nitrogen oxide sensing element 10C in that the nitrogen oxide sensing element 10D is such that a sensing film 11 is formed on the circumference surface of a round rod-like fiber substrate 12d. The constitution other than the nitrogen oxide sensing element 10D is the same as in Embodiment 3.

Figure 12:
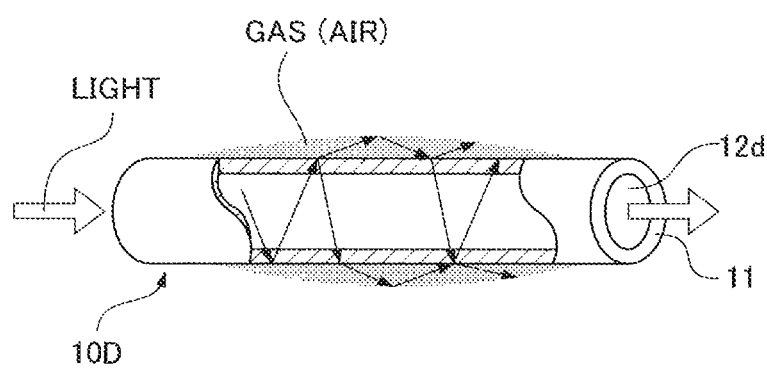
FIG. 12 is an explanatory diagram of light propagation in the same embodiment.

In this nitrogen oxide sensing element 10D, the whole surface of the substrate 12d is coated with the sensing film 11, diffusion light introduced to the end face of the substrate 12d is wave-guided in the film as illustrated in FIG. 12, and is reflected on the interface between the sensing film and the air; the reflected light is also reflected on the interface between the substrate 12d and the sensing film 11 and thus multiple reflection is repeated; consequently, the absorption band responding to the NO gas is amplified and thus the sensitivity to NO can be increased. In contrast to a plate-like light waveguide measurement sensor, light leakage from the side surfaces does not occur and light loss can be reduced, so that optical amplification can be performed efficiently, and thus the improvement of the sensitivity to NO can be realized.

The nitrogen oxide sensing element 10D is fabricated as follows.

First, CoTPP and PEO are added in chloroform to prepare a solution and the solution is stirred to prepare a CoTPP-PEO solution having a CoTPP concentration of $1\times10^{-4}$ mol/L and a PEO concentration of 1 (wt/vol) %. Next, a glass rod (length: 150 mm, diameter: 3 mm, TE-32, manufactured by Iwaki Glass Co., Ltd.) is immersed in the CoTPP-PEO solution for 10 seconds. Then, the substrate is pulled up at an appropriate speed and dried at room temperature. By the above-described method, a sensor device in which the sensing film is formed on the round rod-like substrate is fabricated. As the substrate, polymer fiber such as polymethyl methacrylate (PMMA) fiber and polycarbonate (PC) fiber can also be used.

The procedure of sensing nitrogen oxide by using the light waveguide-type nitrogen oxide concentration determination device shown in FIG. 11 is the same as in Embodiment 3.

When the end face of the nitrogen oxide sensing element 10D is irradiated with diffusion light, the light is repeatedly totally reflected between the substrate 12d and the sensing film 11, and thus the number of times of reflection can be increased. Similarly to the plate-like nitrogen oxide sensing element 10A, the nitrogen oxide sensing element 10D can largely reduce the optical transmittance, and hence can increase the sensitivity to NO. The round rod-like nitrogen oxide sensing element 10D makes it possible to adjust optical components more easily than the plate-like nitrogen oxide sensing element 10A.

In the present embodiment, the end face of the nitrogen oxide sensing element 10D is irradiated with diffusion light, but parallel light can also be used. In the case of parallel light, the end face of the nitrogen oxide sensing element 10D is obliquely irradiated. When the end face of the nitrogen oxide sensing element 10D is irradiated with parallel light, the incident angle effective for the multiple reflection of waves guided in the film can be set by using an optical prism.

In each of the above-described embodiments, the temperature controller 24 for heat treating the sensing film at the time of measurement is placed separately from the nitrogen oxide sensing element 10A, 10B, 10C or 10D. In contrast to these embodiments, in each of the following embodiments, there is used a nitrogen oxide sensor 34A, 34B, 34C or 34D in which a temperature controller 24a for heat treating the sensing film at the time of measurement is placed integrally with the nitrogen oxide sensing element 10A, 10B, 10C or 10D, respectively.

Embodiment 5

Figure 13:
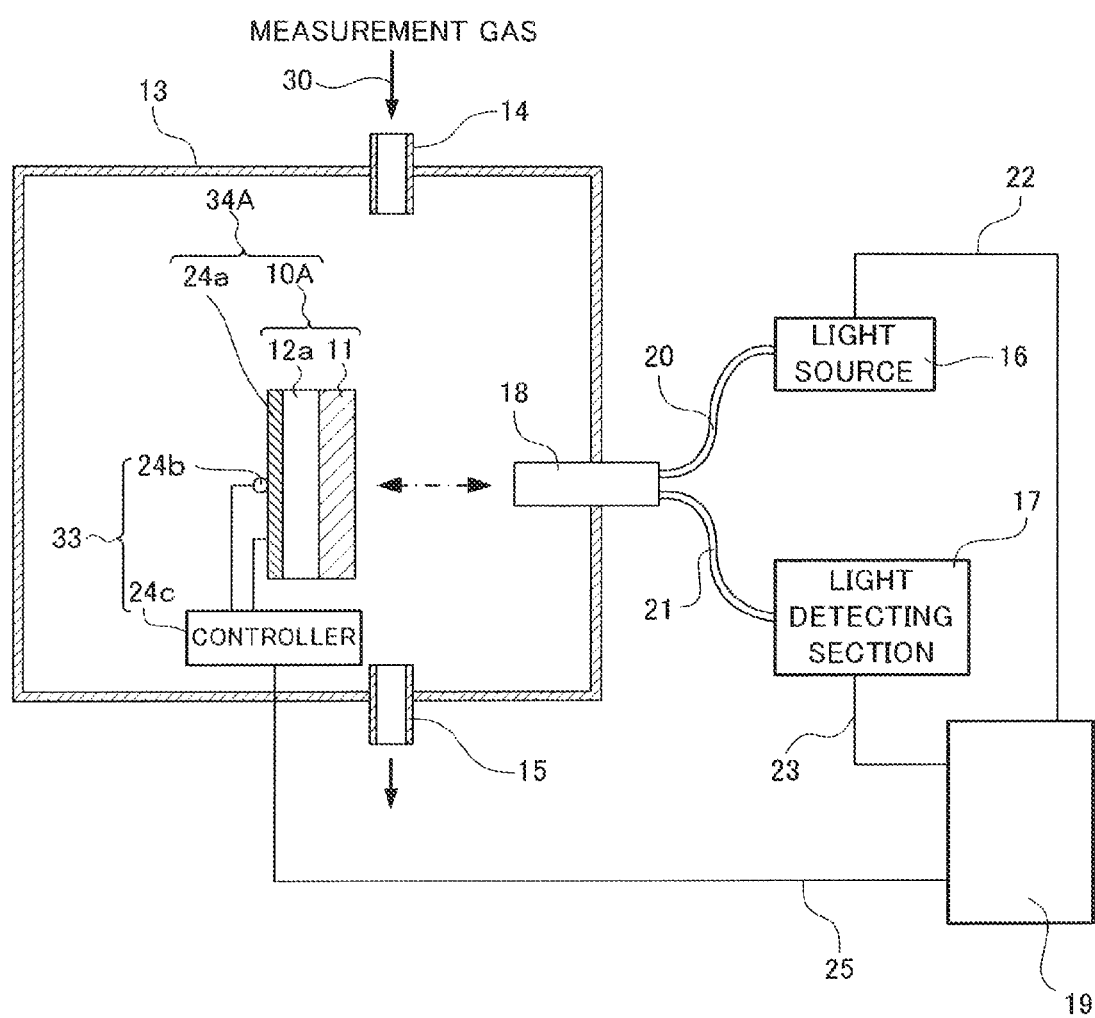
FIG. 13 is a block diagram illustrating a nitrogen oxide concentration determination device using a nitrogen oxide sensor in Embodiment 5 of the present invention.

FIG. 13 illustrates a light reflection-type nitrogen oxide concentration determination device using a nitrogen oxide sensor 34A of the present invention.

The nitrogen oxide sensor 34A is fabricated by integrally forming a heater 24a on a side opposite to the side of a substrate 12a of a nitrogen oxide sensing element 10A, on which a sensing film 11 is formed. The electrical energization of the heater 24a is controlled by a temperature controller 33 for allowing the temperature of the nitrogen oxide sensing element 10A to get closer to a target temperature.

The temperature controller 33 is constituted by a temperature sensor 24b such as a thermocouple for sensing the temperature of the heater 24a and a controller 24c for controlling the electrical energization of the heater to allow the temperature sensed by the temperature sensor 24b to get closer to a target temperature. In the present embodiment, the heater 24a is placed on the side opposite to the side of the substrate 12a, on which the sensing film 11 is formed. Specifically, the heater 24a is a thin film heater, and as a material for the heater, the heretofore known materials such as platinum (Pt), a nichrome alloy (NiCr) and tantalum nitride ($TaN_2$) can be used. Alternatively, a sheathed heater incorporating a nichrome wire as embedded therein may be brought into contact with an alumina substrate 12a.

The nitrogen oxide sensor 34A is set in a measurement cell 13. A measurement gas 30 containing nitrogen oxide is introduced from a gas inlet 14 into the interior of the measurement cell 13 and discharged from a gas outlet 15, and thus the sensing film 11 is exposed to the measurement gas 30.

For the purpose of detecting an optical property change of the sensing film 11 between before and after the sensing film 11 is exposed to the measurement gas 30, in the light reflection-type nitrogen oxide concentration determination device, a light projecting and receiving section 18 is assembled so as to face the nitrogen oxide sensor 34A. More specifically, the light projecting and receiving section 18 perpendicularly irradiates the sensing film 11 of the nitrogen oxide sensing element 10A with light from a light source 16 through an optical fiber 20, and the reflected light passes through the light projecting and receiving section 18 and an optical fiber 21, and is then detected by a light detecting section 17.

The light detecting section 17 is constituted by an optical band pass filter (not shown), a silicon photodiode (not shown), a photocurrent-voltage conversion circuit (not shown) and an amplification circuit (not shown). The reflected light is converted into an optical detection signal corresponding to the reflected light intensity for measurement.

The light source 16, the light detecting section 17 and the controller 24c are connected to a measurement controller 19 through control wires 22, 23 and 25, respectively, for the purpose of controlling the respective operations of the light source, light detecting section and controller.

The nitrogen oxide sensor 34A is fabricated as follows.

The sensing film 11 is formed by dispersing CoTPP, which is a porphyrin containing cobalt as a central metal, in a polyethylene oxide (PEO) polymer (glass transition temperature Tg=−53° C., melting point Tm=68° C., refractive index n=1.46) (hereinafter referred to as a CoTPP-PEO film). The refractive index (hereinafter referred to as n) in an optical wavelength range of 380 nm to 800 nm of the polymer is preferably 1.4 to 1.7. This is because when n is 1.4 to 1.7, the absorbance magnitude is small to be almost transparent and to have a transmittance of 90% or more for the optical wavelength used for nitrogen oxide sensing. The use of such a polymer leads to the below-mentioned absorbance change due to a reaction between the porphyrin containing cobalt as a central metal and the nitrogen oxide, and hence makes it possible to effectively measure a change of the reflected light or the transmitted light.

Additionally, the glass transition temperature (hereinafter referred to as Tg) of the polymer is preferably −150° C. to 150° C. The polymer in such a glass transition temperature range makes it possible to improve the gas permeability and the response to the nitrogen oxide gas by controlling the temperature of the nitrogen oxide sensor 34A.

In the case of a polymer in which Tg is lower than −150° C., at normal temperature, the heat treatment temperature (a first temperature: T1) at the time of the below-mentioned initialization and the sensor temperature (a second temperature: T2) at the time of the below-mentioned NO determination both exceed the melting point Tm of the polymer, the polymer always takes a molten state, and consequently, the sensitivity in sensing the nitrogen oxide is decreased.

On the other hand, when a polymer in which Tg exceeds 150° C. is used, the melting point Tm of the polymer reaches 250° C. or higher, and hence it is necessary to set the heat treatment temperature (the first temperature: T1) at the time of initialization at 250° C. or higher.

For CoTPP, there is a limit temperature. Here, the limit temperature means a temperature at which CoTPP is decomposed, and the limit temperature is defined by a temperature at which weight reduction occurs in the TG (THERMAL GRAVITY) analysis measurement or by a temperature at which the exothermic peak in the DTA (DIFFERENTIAL THERMAL ANALYSIS) occurs (not shown). While a nitrogen gas was being made to flow at a flow rate of 200 ml/min toward the CoTPP used in this instance as a sensing agent, the CoTPP was subjected to the TG analysis. Consequently, the weight reduction started at 293° C., and according to the DTA analysis, the exothermic peak appeared at about 400° C. From both of these results, the weight reduction of the sensing agent starting at 293° C. is found to be due to oxidative decomposition.

Therefore, when the first temperature T1, the initialization treatment temperature of the sensor, is close to the decomposition temperature of CoTPP, about 300° C., the sensor sensitivity is gradually degraded with an increase in treatment time t1.

From the above results, it has been found that: for the purpose of realizing the satisfactory reproducibility of the sensor sensitivity, maintaining the recoverability of the sensor sensitivity and realizing a plurality of times of use of the nitrogen oxide sensor 34A, the first temperature T1 and the second temperature T2, which is a sensor temperature at the time of measurement, are required to be considered according to the limit temperature of CoTPP, which is the material of the sensing film, and the Tg and Tm of the polymer holding the sensing agent, and T1 and T2 are preferably lower.

The absorption band having a central wavelength of 414 nm of Co(II)TPP and the absorption band having a central wavelength of 435 nm of Co(III)TPP in the nitrogen oxide sensing element 10A shown in FIG. 3 are shifted by a few nanometers depending on the polarization condition of the polymer, as the case may be. When the superposition condition of Co(II)TPP and Co(III)TPP occurs, these absorption bands are shifted within the central optical wavelength range as the case may be depending on the occurrence proportions of the above-described band conditions. These 414-nm optical absorption band and 435-nm optical absorption band are both referred to as the Soret band or the B-band, and each have a large molar extinction coefficient. It has been known that there is an absorption band called Q-band which is lower in absorption than the Soret band, in addition to these absorption bands, in the vicinity of an optical wavelength of 530 nm, and further in the vicinity of an optical wavelength of 680 nm. The present inventors have made various investigations under the assumption that for the purpose of measuring low concentration NO at a level of 100 ppb or less, it is effective to utilize the NO responsiveness of the optical absorption band of the Soret band having an absorbance height larger by a factor of about four than the absorbance height of the Q-band at the optical wavelength of 530 nm.

The change magnitudes of these absorption bands depend on the NO concentration, and hence, from the magnitudes of changes of the absorption bands of CoTPP caused by the exposure to NO, the NO concentration can be determined. The change of the absorption band can be determined by measuring the reflection spectra of the sensing film before and after the exposure to NO. As described above, by using CoTPP, the NO concentration can be determined.

However, the nitrogen oxide sensing element 10A fabricated by the above-described method usually reacts with $O_2$ or CO in the air, and the absorption band of Co(III)TPP containing trivalent cobalt becomes a predominating component, resulting in an absorption band superposed with the absorption band of Co(II)TPP containing divalent cobalt. The reflection spectrum absorption band of an untreated nitrogen oxide sensor 34A is shown as condition 1 in FIG. 14. In an untreated sensing film 11, Co(III)TPP is the main component, and NO cannot be determined. CoTPP capable of reacting with NO is restricted to Co(II)TPP containing divalent cobalt as a central metal. When the maximum absorption wavelength is 435 nm, the proportion of Co(II)TPP capable of reacting with NO is small, and consequently, an extremely small amount of NO cannot be determined with satisfactory accuracy. The present inventors made various diligent studies, and consequently have discovered that an extremely low concentration of nitrogen oxide gas at a level of 5 ppb can be determined by changing CoTPP to Co(II)TPP containing divalent cobalt and performing the pretreatment of the sensing film 11 so as to yield the optical absorption band of the condition 3 of FIG. 14, immediately before the determination of the nitrogen oxide gas.

Hereinafter, the initialization treatment and the temperature control method at the time of determination of the NO gas are described.

Figure 15:
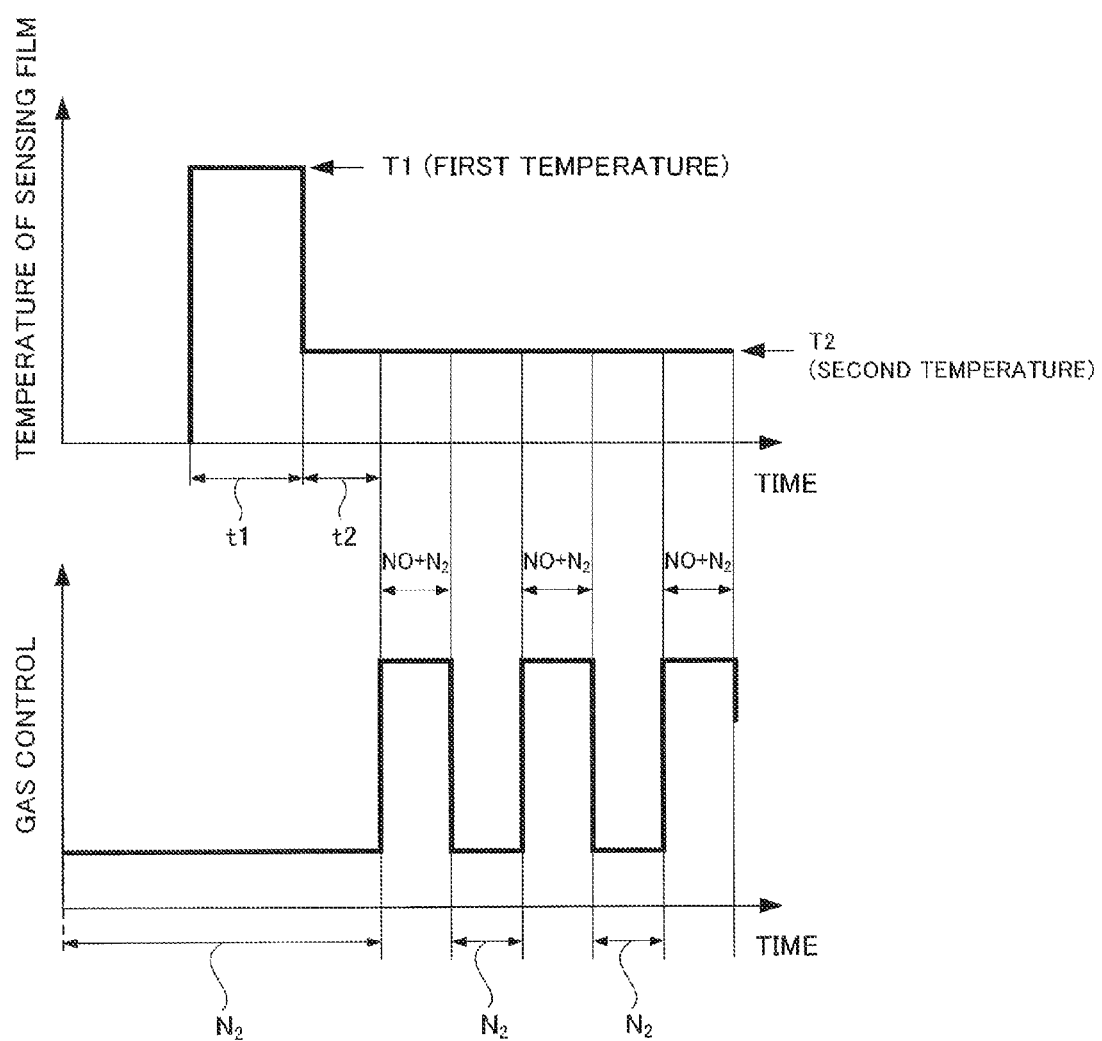
FIG. 15 is a chart showing the temperature control timing of the nitrogen oxide concentration determination device in the same embodiment.

FIG. 15 shows a timing chart for the pretreatment of the sensing film 11 and the determination using the nitrogen oxide sensor 34A.

The sensing film 11 is irradiated with sensing light from the light source 16 through the optical fiber 20 and the light projecting and receiving section 18. The irradiation with the sensing light is continued until the end of the determination. The light source 16 is preferably such a light source that covers an optical wavelength region from 400 nm to 450 nm. This is because the CoTPP-PEO film 11 of the sensing film 11 has, as described above, an absorption band having a large molar extinction coefficient, called the Soret band or the B-band, in this optical wavelength region.

Figure 14:
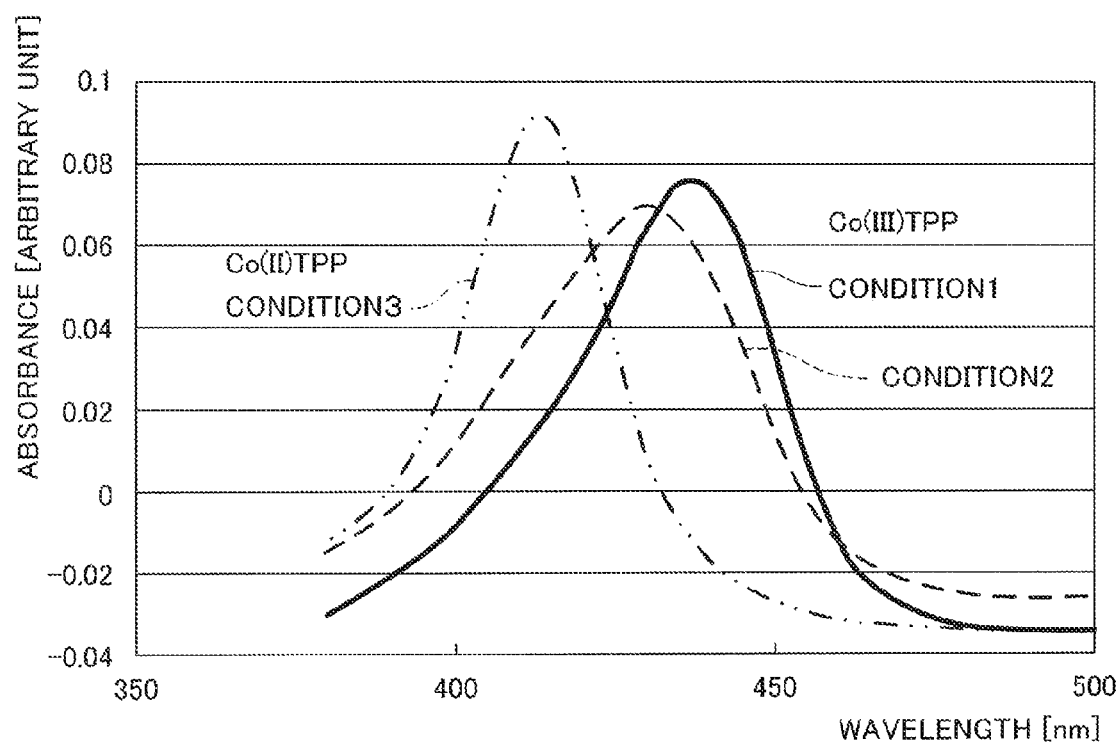
FIG. 14 shows the optical absorption spectra of different states of a nitrogen oxide sensing element in the same embodiment.

When the CoTPP-PEO film of the sensing film 11 is heated at the first temperature T1 for the predetermined time t1, the molecule of a gas such as $O_2$ or CO bonded to the CoTPP is detached, and along with the detachment, the cobalt of the CoTPP is reduced to result in Co(II)TPP containing divalent cobalt, as illustrated in FIG. 14, starting from the condition 1, passing through the condition 2, and resulting in the condition 3. In this connection, FIG. 4 shows absorbance changes at 414 nm and 435 nm of CoTPP, when the heat treatment of the nitrogen oxide sensor 34A composed of the CoTPP-PEO sensing film was performed under the conditions that: the first temperature T1 in the initialization treatment was set at T1=150° C. so as to be lower than the limit temperature of 290° C. of CoTPP and higher than the melting point of 68° C. of PEO; and a nitrogen gas ($N_2$) as a purge gas was being made to flow at a flow rate of 200 ml/min.

The following has been verified: at the start of heating at 150° C., the absorbance of peak of the absorption band due to Co(III)TPP having a central wavelength of 435 nm is decreased, and on the other hand, the absorbance of peak of the absorption band due to Co(II)TPP having a central wavelength of 414 nm is increased. It has been verified that in about three minutes from the start of heating, the absorbances at both of these wavelengths are saturated, and the absorption band of Co(II)TPP having a peak at the maximum absorption wavelength of 414 nm is obtained (the condition 3 in FIG. 14).

Figure 16:
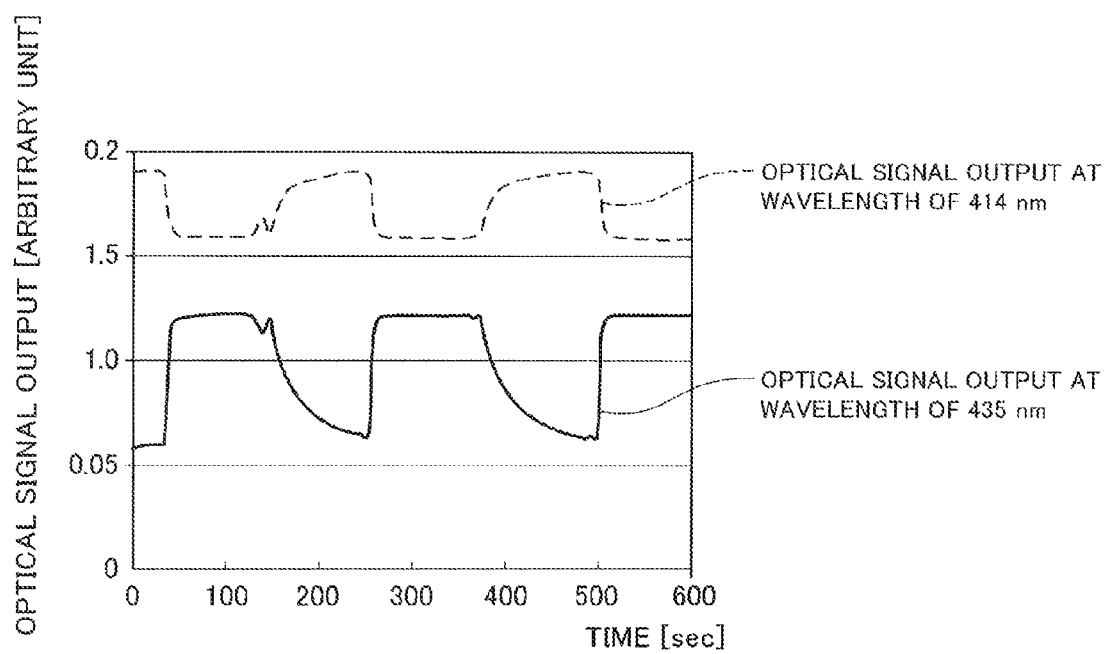
FIG. 16 is an explanatory chart illustrating optical signal outputs when NO of 1 ppm was detected on the basis of the heat treatment timing chart of FIG. 15 by using the nitrogen oxide concentration determination device in the same embodiment.

Next, according to the timing chart of FIG. 15, the exposure to the NO gas was performed under the conditions that while a nitrogen gas ($N_2$) as a purge gas was being made to flow at a flow rate of 200 ml/min as described above, the temperature of the CoTPP-PEO film was decreased by the temperature controller 33 to the predetermined second temperature T2 and maintained for a time t2. The second temperature T2 was set at a temperature of T2=60° C. which was higher than the Tg=−53° C. of PEO and lower than the melting point Tm=68° C. of PEO. FIG. 16 shows an optical signal output (absorbance response) at the optical wavelength of 414 nm and an optical signal output (absorbance response) at the optical wavelength of 435 nm in the nitrogen oxide sensor 34A when the nitrogen oxide sensor 34A was intermittently exposed to a NO gas (base: nitrogen, concentration: 1 ppm, flow rate: 200 ml/min). For the absorbance measurement, a multichannel photodetector system (MCPD-7000, manufactured by Otsuka Electronics Co., Ltd.) was used. Here, the optical signal output (arbitrary output) is given in terms of the absorbance (=Log(100/reflectivity)).

During times other than the exposure to NO, the base gas, namely a nitrogen gas, is made to flow at a flow rate of 200 ml/min. From FIG. 16, it has been verified that by exposing to the NO gas after the CoTPP-PEO film is stabilized at the second temperature T2, the nitrogen oxide gas can be sensed with high accuracy and satisfactory reproducibility.

In this way, the nitrogen oxide sensor 34A enables an increase in the sensitivity to NO by reducing cobalt in CoTPP to divalent cobalt with low temperature heat treatment for an extremely short time. Additionally, because of the operation temperature set at a relatively low temperature, the NO sensing reproducibility can be improved. In other words, by using the heat treatment at a relatively low temperature, highly accurate NO determination can be performed with satisfactory recoverability and with satisfactory reproducibility at a low operation temperature.

When the pretreatment temperature is decreased to T1=50° C. in the heat treatment, the time t1 taken for changing CoTPP so as to have divalent cobalt is extended; however, after a predetermined time has elapsed, the nitrogen oxide sensing element 34A having the sensing film 11 exhibiting the absorption band shown in FIG. 14 is obtained. On the other hand, when the first temperature T1 as the pretreatment temperature is set at 250° C. or higher, the absorbance is decreased over the whole involved wavelength range probably because of the degradation of CoTPP or the PEO polymer.

Accordingly, the CoTPP-PEO film can be recovered in a shorter time to the film containing Co(II)TPP as the main component, by setting the first temperature T1 as the pretreatment temperature of the CoTPP-PEO film at a temperature lower than 290° C., the limit temperature of the sensing film 11, and higher than the melting point Tm of the polymer containing CoTPP dispersed therein. Further, from the viewpoint of suppression of the degradation, the first temperature T1 is preferably set at a temperature higher by about 50° C. than the melting point of the polymer used in the sensing film 11.

The temperature control effect of the CoTPP-polymer film is described in more detail by using the conceptual diagram of the sensing film 11 shown in FIG. 5.

The glass transition temperature of PEO 1 is as low as −53° C.; hence, at normal temperature (for example, 20° C.) PEO 1 is in a glassy state, and the amorphous molecules constituting the glassy state undergo free vibration. In the PEO 1 film, there is a large free space 3 which is not occupied by atoms (or molecules). A part of CoTPP dispersed in PEO 1 is exposed to the free space forming the free volume of the polymer, and repeatedly migrates slow into the interior of the polymer. Usually, it is the CoTPP exposed to the surface of the polymer that is high in the reactivity to the gas (surface reaction). In the case of the CoTPP in the interior of the polymer which is not exposed to the surface of the polymer, the gas diffuses in the polymer, and hence the reactivity to NO is lower than in the case of the surface reaction (diffusion reaction). Accordingly, for the purpose of improving the reactivity by shortening the migration period of CoTPP, it is necessary that the content of Co(II)TPP containing divalent cobalt to be bonded to NO be increased, and at the same time, the Co(II)TPP be made to migrate to the surface of the polymer as much as possible, and thus the collision probability between Co(II)TPP and the NO gas be increased. Therefore, it is recommended that the sensing film 11 be heated at the first temperature T1 free from the polymer degradation so as to increase the Co(II)TPP concentration in the sensing film.

By increasing the operation temperature, the gas selectivity is also improved. The bonding of $O_2$ gas or CO gas to CoTPP is weaker than the bonding of nitrogen oxide to CoTPP, and hence by setting the sensing film temperature T2, the selectivity of the NO gas against $O_2$ gas or CO gas is developed. The temperature T2, which is a measurement temperature, may be set by considering preference between the sensitivity of the sensor and the response speed of the sensor; the second temperature T2 is preferably set at such a high temperature that is at the lowest a temperature higher than the glass transition temperature Tg of the polymer serving as the dispersion medium of the CoTPP sensing agent, and is not influenced by the temperature in the surrounding of the determination device.

Figure 17:
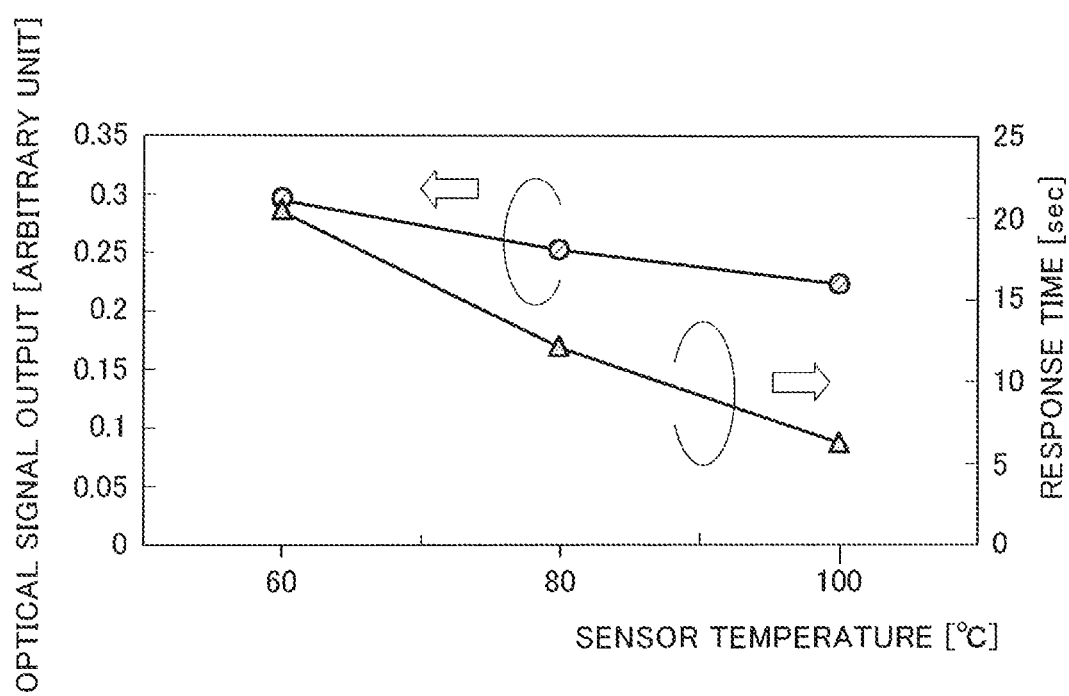
FIG. 17 is a graph showing the dependence of the optical signal output and the dependence of a response time on a sensor temperature T2 when the nitrogen oxide concentration determination device in the same embodiment was used and the sensor temperature T2 was varied to be 60° C., 80° C. and 100° C. by using a temperature controller.

FIG. 17 shows the dependence of the optical signal output and the dependence of the response speed on the second temperature T2, which is the sensor temperature, for the nitrogen oxide sensor 34A including the CoTPP-PEO film, at the time of determining the NO gas. The optical signal output (absorbance) in FIG. 17 was measured by a multichannel photodetector system (MCPD-7000, manufactured by Otsuka Electronics Co., Ltd.).

The second temperature T2 at the time of determining the NO gas concentration was set at 60° C., 80° C. and 100° C. At the measurement at the respective second temperatures T2, heat treatment was performed at the initialization treatment temperature (first temperature T1). The initialization conditions are such that, as described above, the flow rate of nitrogen gas is 200 ml/min, T1=150° C. and t1=10 minutes. The NO gas concentration determination involves a nitrogen base gas, 1 ppm NO, and a flow rate of 200 ml/min. The response speed is defined by a response time taken to go from 10% to 90% of the square optical signal output at the time of the first exposure to the NO gas. From FIG. 17, in the case of an extremely small amount of the NO gas, T2 is preferably 60° C., and in such a case, the response time is made slow. On the other hand, for the purpose of further shortening the determination time, the second temperature T2 is preferably 100° C., and in such a case, the extent of the gas detachment is large and the optical signal output is found to become slightly smaller.

Further, PEO 1 dispersing and holding CoTPP has an effect of preventing the aggregation of CoTPP 2. When PEO 1 is not contained, almost all the CoTPP 2 molecules tend to mutually aggregate, and the amount of CoTPP which can be held in the substrate is small, so that the sensitivity to the NO gas of the sensing film cannot be increased.

The polymer is not limited to PEO, and has only to be a polymer which is transparent or nearly transparent for the measurement optical wavelengths as described above, has a low glass transition temperature and prevents the aggregation of CoTPP. The lower limit of the glass transition temperature Tg is preferably as low as possible from the viewpoint that the power consumption of the nitrogen oxide concentration determination device is suppressed to low-power; however, the polymer is preferably solid at normal temperature, and specifically the lower limit of the glass transition temperature Tg is −150° C. or higher. The upper limit of Tg is preferably such that the heat treatment of the polymer does not affect the properties of CoTPP, and thus, the upper limit of Tg is 150° C.

Accordingly, examples of polymers satisfying the above-described conditions other than PEO (n=1.46, Tg=−53° C., Tm=68° C.) may include: acrylic resins such as polyisobutyl methacrylate (n=1.42, Tg=48° C., Tm=140° C.), polymethyl acrylate (n=1.49, Tg=66° C.) and polyacrylonitrile (n=1.52, Tg=97° C.); vinyl resins such as polystyrene (n=1.59, Tg=100° C.), polyvinyl chloride (n=1.63, Tg=81° C.) and polyvinyl alcohol (n=1.49, Tg=85° C.); polydimethylsiloxane (n=1.42, Tg=−123° C.); and ethyl cellulose (n=1.47, Tg=43° C., Tm=200° C.). Some of the above-described polymers do not have any definite melting points, and as for the initialization temperature, the initialization is preferably performed at a temperature higher by about 150° C. than the glass transition temperature Tg.

Here, the following points are the same as described above: these resins include copolymers for copolymerizable resins and modified resins for resins modifiable with side chain substituents for the purpose of improving the refractive index or the heat resistance; additionally, for the purpose of improving the fluidity, the above-described polymers may include plasticizers.

Next, the reactivity between CoTPP and the analyte gas is described.

The reactivity between CoTPP and the analyte gas is determined by the relationship between the electronic states of CoTPP and the analyte gas. Specifically, the reactivity is determined by the magnitude of a redox potential difference determined by the electronic states of CoTPP and the analyte gas, and a change of the optical absorption band of CoTPP occurs depending on the redox reaction. Because the present inventors have discovered that the reactivities of CoTPP with other gases are low as compared to the reactivity of CoTPP with a nitrogen oxide gas NOx such as NO and $NO_2$, it is inferred that the redox potential difference between CoTPP and NOx is smaller as compared to redox potential differences between CoTPP and other gases, and thus the reactivity between CoTPP and NOx is high. The present inventors have verified that after heat treatment, the reactivity to $O_2$ or CO, a reaction inhibitor, is extremely lower as compared with the reactivity to NOx, and hence, the divalent state of CoTPP can be maintained in the sensing film of the present invention within at least 10 minutes without exposure to the NOx gas. Therefore, the nitrogen oxide gas can be extremely effectively sensed by performing exposure to the nitrogen oxide gas under the condition that reduction to Co(II)TPP containing divalent cobalt is performed by initialization based on pretreatment to the nitrogen oxide gas.

As is the case with Embodiment 1, the NO sensing agent is not limited to CoTPP, and has only to be any of a porphyrin containing cobalt as a central metal and undergoing a change of the absorption band thereof due to the bonding of NO thereto, a single derivative having a porphyrin skeleton containing cobalt as a central metal and undergoing a change of the absorption band thereof due to the bonding of NO thereto, and a mixture of derivatives each having a porphyrin skeleton containing cobalt as a central metal and undergoing a change of the absorption band thereof due to the bonding of NO thereto.

The CoTPP dispersed in the polymer of the sensing film 11 undergoes, as described above, changes in the absorption spectrum thereof when exposed to the nitrogen oxide gas, and hence, by measuring the reflectivity of the sensing film 11 before and after the exposure to the gas, the nitrogen oxide concentration in the measurement gas can be derived.

A method for fabricating the nitrogen oxide sensing element 10A is the same as in Embodiment 1.

The thickness of the sensing film 11 is set according to the reactivity of the sensing film to the nitrogen oxide gas. When the CoTPP concentration is constant, the sensitivity is increased with an increase in the film thickness, but the gas diffusion time is extended, and the response to the nitrogen oxide gas is made slow. When the thickness of the sensing film is thin, the sensing film is degraded with an increasing number of times of use.

In the above-described constitution, details of the practical procedure of the concentration sensing of the nitrogen oxide gas are as follows.

First, for the purpose of determining the NO concentration with satisfactory accuracy, heat treatment for changing CoTPP to CoTPP containing divalent cobalt is performed by using the heater 24a. The heat treatment is performed for a predetermined time under heat treatment conditions such that the first temperature T1 is lower than the limit temperature of CoTPP of 250° C. and equal to or higher than the melting point Tm of the polymer. In the case of the PEO polymer, Tm=68° C., and hence T1 is preferably 70° C. to 150° C. Although t1 is dependent on the thermal design of the nitrogen oxide sensor 34A, when T1=150° C., t1 of 3 minutes or more is sufficient under the conditions that an alumina substrate (area: 10 mm$^2$, thickness: 0.7 mm) is used, the measurement cell volume is 500 mm$^3$ and the purge gas flow rate is 200 ml/min.

Next, the temperature of the sensing film 11 is set at the second temperature T2, as the measurement temperature, so as to be higher than the glass transition temperature Tg of the polymer and the temperature in the surrounding atmosphere, for example, at T2=80° C. in the case of PEO; after t2=3 minutes when the sensing film temperature is stabilized, NO, the measurement gas is introduced from the gas inlet 14 into the measurement cell 13. The stabilization time t2 may be set in consideration of the sensing device and the gas flow rate. The specific set time is set at a time when the optical signal output of the sensor is stabilized. When NO is adsorbed to the CoTPP of the sensing film 11, an electron is transferred from the cobalt of the CoTPP to NO to oxidize the CoTPP, so that in the optical reflection spectrum, the absorption band at the wavelength of 414 nm is decreased in intensity, and consequently the optical reflectivity at the wavelength of 414 nm is increased. At the same time the absorption band at the wavelength of 435 nm is increased in intensity, and consequently the optical reflectivity at the wavelength of 435 nm is decreased.

FIG. 6 shows a time change of the optical signal output observed when the light reflection measurement sensor 10A was alternately exposed with a period of 2 minutes to NO gas (base: nitrogen, concentration: 1 ppm, flow rate: 200 ml/min, T2=80° C.) and nitrogen gas (flow rate: 200 ml/min).

From FIG. 6, it is found that the absorption spectrum of the CoTPP in the sensing film is changed largely when the sensing film is exposed to the NO gas, the corresponding optical signal output is changed and the sensor response reaches a stationary value in a time as extremely short as about 10 seconds.

Next, by using, as the light detecting section 17, an optical band pass filter (not shown) meeting the above-described change of the optical absorption band, a silicon photodiode (not shown), a photocurrent-voltage conversion circuit (not shown) and an amplification circuit (not shown), the optical sensing signal (voltage) was measured with NO gas concentrations varied from 5 ppb to 10 ppm.

The relation between the differential output between the optical signal output of the initialized sensing film 11 and the optical signal output of the sensing film 11 exposed to the NO gas and the NO gas concentration was the same as shown in FIG. 7. From this figure, it is found that by using the nitrogen oxide sensor 34A, the NO concentration can be determined in the NO concentration range from 5 ppb to 10 ppm. Although FIG. 6 and FIG. 7 are different from each other in numerical values on the ordinate, it has been verified that the same sensor shows the same tendency.

In the measurement controller 19, the characteristic curve of a calibration curve required for the determination of concentration of an analyte gas (=measurement gas) having an unknown concentration or the mathematical expression specifying the characteristic curve of the calibration curve is written as follows.

When data for the calibration curve are collected, as the pretreatment of the nitrogen oxide sensor 34A, heat treatment is performed at a first temperature of T1=150° C. for t1=10 minutes, and thus the CoTPP dispersed in the polymer is initialized to CoTPP containing divalent cobalt as a central metal; then, successively, an operation is performed for the interior of the measurement cell 13 to be set at the second predetermined temperature of T2=80° C., the sensing film 11 is irradiated with light having a central wavelength of 430 nm from the light source 16, an optical signal output V1 from the initialized sensing film 11 is measured and the measured value is stored in the measurement controller 19.

Successively, under the condition that the nitrogen oxide sensor 34A is set at the second temperature T2=80° C., a NO gas (base: nitrogen, concentration: 5 ppb, flow rate: 200 ml/min) is made to flow toward the sensing film 11 for 10 seconds, and the optical signal output at the elapsed time of 10 seconds is measured to obtain a second optical signal output V2 (5 ppb). In the measurement controller 19, the measurement results are stored as the following differential output:

$$\text{differential output } \Delta V(5\text{ ppb})1 = V2(5\text{ ppb}) - V1$$

With the same gas concentration, a set of the initialization, the exposure to the NO gas and the measurement is repeated four more times to measure $\Delta V(5\text{ ppb})2$ to $\Delta V(5\text{ ppb})5$, and thus, with the same gas concentration, five times of measurement are performed in total.

Under the same conditions except for the NO gas concentration, the optical signal output is measured at each of the following NO gas concentrations: 10 ppb, 50 ppb, 100 ppb, 500 ppb and 1 ppm; thus a calibration curve between the NO gas concentration and the optical signal output is obtained and stored in the measurement controller 19.

The change curve of the differential output $\Delta V$ corresponding to the gas concentration is obtained in the measurement controller 19, on the basis of data obtained from measurement with the known gas concentrations, and the curve thus obtained is established as the characteristic curve of the calibration curve.

The concentration of the analyte gas is determined as follows, with reference to the characteristic curve of the calibration curve stored in the measurement controller 19 as described above, or the mathematical expression specifying the characteristic curve of the calibration curve.

Also when the analyte gas undergoes measurement, heat treatment is performed at T1=150° C. for t1=10 minutes before the analyte gas undergoes measurement, and thus the CoTPP dispersed in the polymer is initialized to CoTPP containing divalent cobalt as a central metal.

Successively, after the temperature of the nitrogen oxide sensor 34A is set at the second temperature of T2=80° C., then the sensing film 11 is irradiated with sensing light from the light source 16 having a central wavelength of 430 nm, and the optical signal output V1 of the initialized sensing film 11 is measured and the measured value is stored in the measurement controller 19.

Successively, with the nitrogen oxide sensor 34A set at the second temperature of T2=80° C., the analyte gas (flow rate: 200 ml/min) is made to flow toward the sensing film 11 for 10 seconds, and the optical signal output at the elapsed time of 10 seconds is measured to obtain an optical signal output V2(X). In the measurement controller 19, the following differential output at the time of measurement of the analyte gas is calculated from the above-described optical signal outputs:

$$\text{differential output } \Delta V(X) = V2(X) - V1$$

Next, the gas concentration can be read out on the basis of the differential output $\Delta V(X)$ as a key, with reference to the characteristic curve of the calibration curve calculated beforehand and stored in the measurement controller 19, or the NO gas concentration of the analyte gas can be calculated by substituting the calculated differential output into the mathematical expression specifying the characteristic curve of the calibration curve.

As described above, first at the time of measurement, the heat treatment for initializing the sensing film 11 is performed; then, the reflected light being reflected on the sensing film 11 and coming back therefrom is detected by the light detecting section 17 under the condition before the exposure of the sensing film 11 to the NO gas (analyte gas); the optical output V1 at this time from the output of the light detecting section 17 is measured; then the reflected light being reflected on the sensing film 11 and coming back therefrom is detected by the light detecting section 17 under the condition that the sensing film 11 is being exposed to the NO gas (analyte gas); the optical output V2(X) at this time from the output of the light detecting section 17 is measured; and on the basis of data of the calibration curve and the differential output $\Delta V(X) = V2(X) - V1$, the NO concentration can be measured with high sensitivity over a wide concentration range.

In the present embodiment, the heat treatment temperature, the treatment time and the standard gas concentrations used at the time of preparation of the calibration curve are not limited, and the nitrogen oxide concentration can be determined over a range from 5 ppb to 10 ppm by making the CoTPP dispersed in the polymer contain divalent cobalt, and by making constant the heat treatment temperature, the treatment time and the gas flow rate condition at the time of preparation of the calibration curve.

In the case of the light reflection-type nitrogen oxide determination device shown in FIG. 13, a non-light-transmitting opaque substrate is used for the substrate 12a; however, it is also possible to make a light reflection-type nitrogen oxide determination device by using the nitrogen oxide sensor 34A, which is fabricated by using a translucent substrate as the substrate, forming on the translucent substrate a film having a surface condition capable of obtaining light reflection, for example, a metal film with a thickness sufficient to block light transmission, and forming the sensing film 11 on the metal film. Further, in the case of a metal plate, when the surface condition of the metal plate is capable of obtaining light reflection, it is possible to make a light reflection-type nitrogen oxide concentration determination device by using the nitrogen oxide sensor 34A fabricated by forming the sensing film 11 on the metal plate.

Moreover, in the case of the light reflection type nitrogen oxide concentration determination device shown in FIG. 13, the sensing film 11 is irradiated with light from the light projecting and receiving section 18, and the reflected light can be detected by the light projecting and receiving section 18, so that there is a feature that the assembling of optical components is easy.

As the heater 24a, heaters such as a ceramic heater, a sheath heater and a thin film heater can be used. In the case of a thin film heater, the thin film heater is formed by heretofore known techniques, namely, a film formation technique, photolithography and etching. The thin film heater can be formed of thin film material made of any of nickel (Ni), chromium (Cr) and tantalum (Ta), any of alloys between these, any of metal oxides of these, or any of metal nitrides of these.

Figure 18:
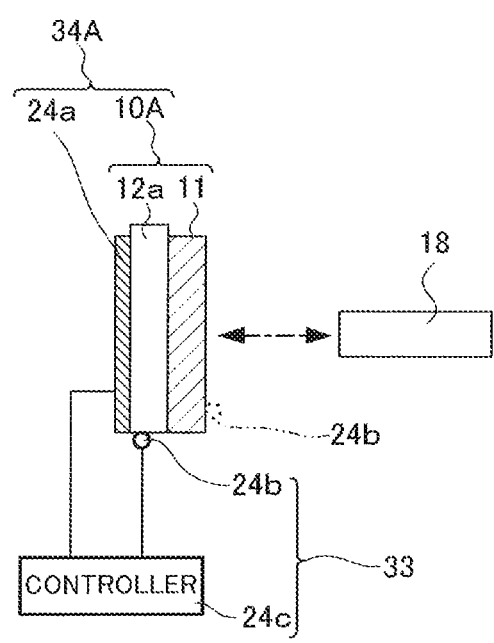
FIG. 18 is an explanatory diagram illustrating another arrangement of a heater 24a and a temperature sensor 24b in the same embodiment.

The temperature of the sensing film 11 has been indirectly sensed by bringing the temperature sensor 24b into direct contact with the heater 24a; however, the concerned configuration may be either of the following: as shown in FIG. 18, the temperature sensor 24b is brought into contact with the substrate 12a to indirectly sense the temperature of the sensing film 11; and, as indicated by a broken line in FIG. 18, the temperature sensor 24b is brought into direct contact with the sensing film 11 to sense the temperature of the sensing film 11.

The above description has been given on the assumption that the sensing film 11 is continuously irradiated with sensing light until the end of measurement; however, when the attenuation of the light due to the sensing film 11 is large, it is necessary to increase the power of light irradiating the substrate 12a through the sensing film 11; in this case, if continuous light irradiation is performed, heat input into the sensing film 11 or the substrate 12a becomes large, so that it is preferable to measure the optical signal outputs V1 and V2 by intermittently irradiating the substrate 12a through the sensing film 11.

Embodiment 6

Figure 19:
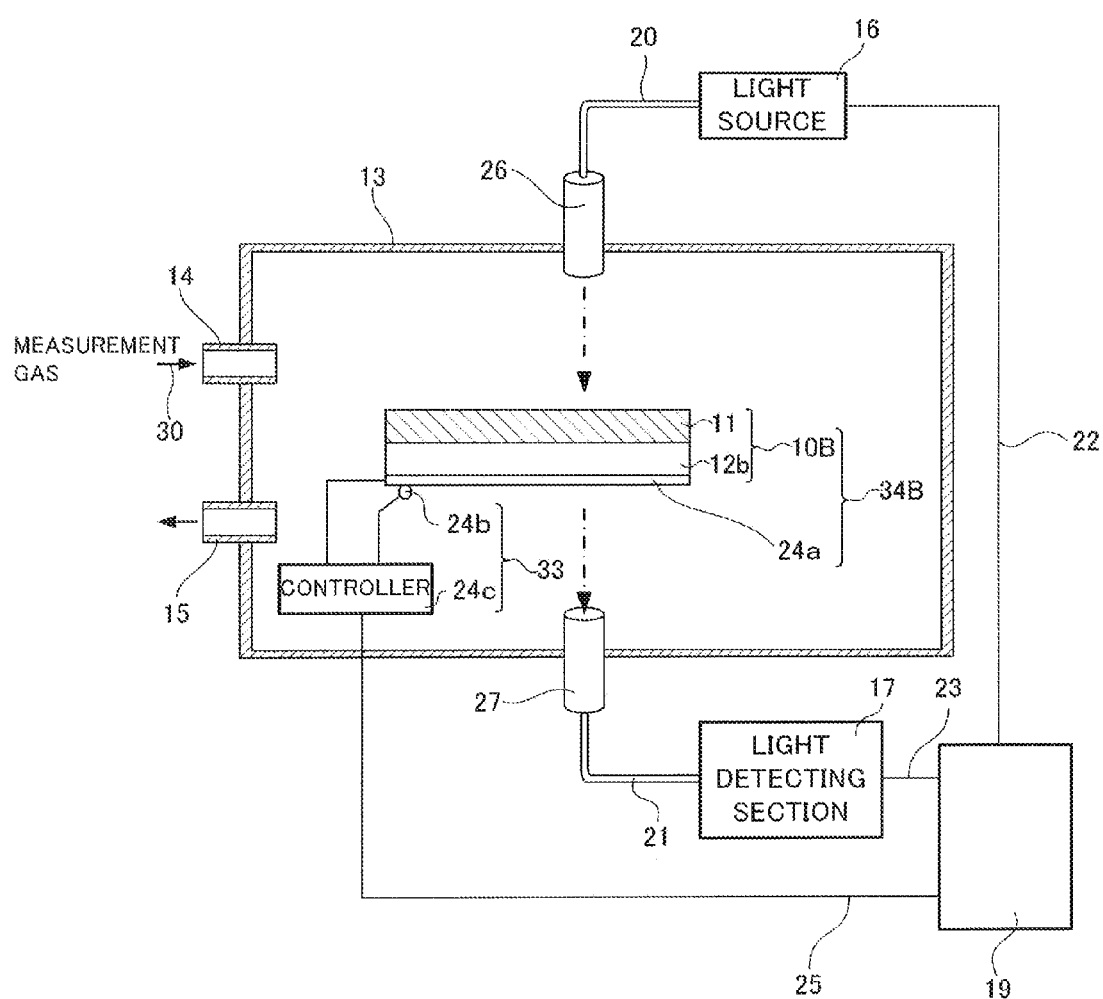
FIG. 19 is a block diagram illustrating a nitrogen oxide concentration determination device using a nitrogen oxide sensor in Embodiment 6 of the present invention.

FIG. 19 illustrates a nitrogen oxide sensor 34B using a nitrogen oxide sensing element 10B of the present invention and a light transmission-type nitrogen oxide concentration determination device using the nitrogen oxide sensor 34B.

In the case of the light reflection-type nitrogen oxide concentration determination device of Embodiment 5, used are the nitrogen oxide sensor 34A fabricated by forming the sensing film 11 on the non-light-transmitting substrate 12a or by forming the sensing film 11 on a film having a surface condition capable of obtaining light reflection, the film being formed with a thickness sufficient to block light transmission on a translucent substrate; however, Embodiment 6 is different from Embodiment 5 in that, in Embodiment 6, sensing light transmits a sensing film 11 and a substrate 12b.

In the nitrogen oxide sensor 34B, a heater 24a is placed on a side opposite to the side of the nitrogen oxide sensing element 10B of Embodiment 2, on which the sensing film 11 is formed. In the present embodiment, the heater 24a is a transparent or nearly transparent thin film heater which sensing light transmits. Otherwise, the structure and fabrication method are the same as in the above-described nitrogen oxide sensor 34A of Embodiment 5.

A measurement gas 30 is introduced from a gas inlet 14 into a measurement cell 13, the sensing film 11 is exposed to the measurement gas 30, and the measurement gas is discharged from a gas outlet 15.

A temperature controller 33 for allowing the temperature of the nitrogen oxide sensor 34B to get closer to a target temperature is constituted by a temperature sensor 24b such as a thermocouple and a controller 24c for controlling the electrical energization of the heater 24a so as to allow a temperature sensed by the temperature sensor 24b to get closer to the target temperature.

As a material for the transparent or nearly transparent thin film heater, heretofore known indium oxide ($In_2O_3$), tin oxide ($SnO_2$), ITO which is a composite film of indium and tin, or zinc oxide (ZnO) can be used. Films of these materials can be formed, with masking, by physical vapor deposition such as reactive sputtering and reactive ion plating. Additionally, heretofore known photolithography is performed after vapor deposition to etch unnecessary parts, so that thin film heaters can be formed.

First, CoTPP and PEO are added in chloroform to prepare a solution and the solution is stirred to prepare a CoTPP-PEO solution having a CoTPP concentration of $1 \times 10^{-4}$ mol/L and a PEO concentration of 1 (wt/vol) %.

Next, the CoTPP-PEO solution is applied by spin coating onto the back side of a glass plate on which a transparent thin film heater prepared by the heretofore known technology is formed, and is dried to prepare the sensing film 11.

The CoTPP in the nitrogen oxide sensor 34B undergoes a change of the absorption spectrum thereof when exposed to nitrogen oxide, and hence the nitrogen oxide concentration in the measurement gas can be derived by measuring the optical transmittances of the sensing film 11 before and after the exposure of the sensing film 11 to the measurement gas 30.

Light emitted from a light source 16 passes through an optical fiber 20 and a light projecting section 26, and then irradiates the nitrogen oxide sensor 34B; the light transmitting the nitrogen oxide sensor 34B passes through a light receiving section 27 and an optical fiber 21, and is then detected by a light detecting section 17. The light detecting section 17 is constituted by an optical band pass filter (not shown), a silicon photodiode (not shown), a photocurrent-voltage conversion circuit (not shown) and an amplification circuit (not shown).

The concerned arrangement is such that light radiating from the light projecting section 26 is perpendicularly incident on the nitrogen oxide sensor 34B, and the light transmitting the nitrogen oxide sensor 34B irradiates the light receiving section 27. The light source 16, the light detecting section 17 and the temperature controller 33 are connected to a measurement controller 19 through control wires 22, 23 and 25, respectively, for the purpose of controlling the respective operations of the light source, light detecting section and temperature controller. The sensing procedure of the nitrogen oxide gas concentration is the same as that in Embodiment 5. As compared to the reflection type of Embodiment 5, the transmission type of Embodiment 6 can reduce by half the optical path length, and hence can reduce the scattering loss and increase the output.

Figure 20:
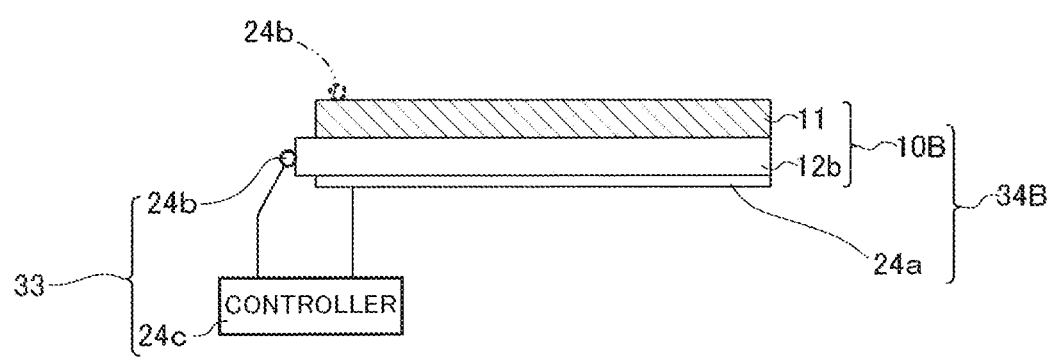
FIG. 20 is an explanatory diagram illustrating another arrangement of a heater 24a and a temperature sensor 24b in the same embodiment.

The temperature of the sensing film 11 is indirectly sensed by bringing the temperature sensor 24b into direct contact with the heater 24a; however, the concerned configuration may be either of the following: as shown in FIG. 20, the temperature sensor 24b is brought into contact with the substrate 12b and thus the temperature of the sensing film 11 may be indirectly sensed; and, as indicated by a broken line in FIG. 20, the temperature sensor 24b is brought into direct contact with the sensing film 11, and thus the temperature of the sensing film 11 may be sensed.

Also in the case of Embodiment 6, the sensing film 11 is continuously irradiated with sensing light until the end of the measurement; however, when the attenuation of the light due to the sensing film 11 is large, it is necessary to increase the power of light irradiating the sensing film 11; in this case, if continuous light irradiation is performed, heat input into the sensing film 11 or the substrate 12b becomes large, and hence it is preferable to measure the optical signal outputs V1 and V2 by intermittently irradiating the sensing film 11.

Embodiment 7

Figure 21:
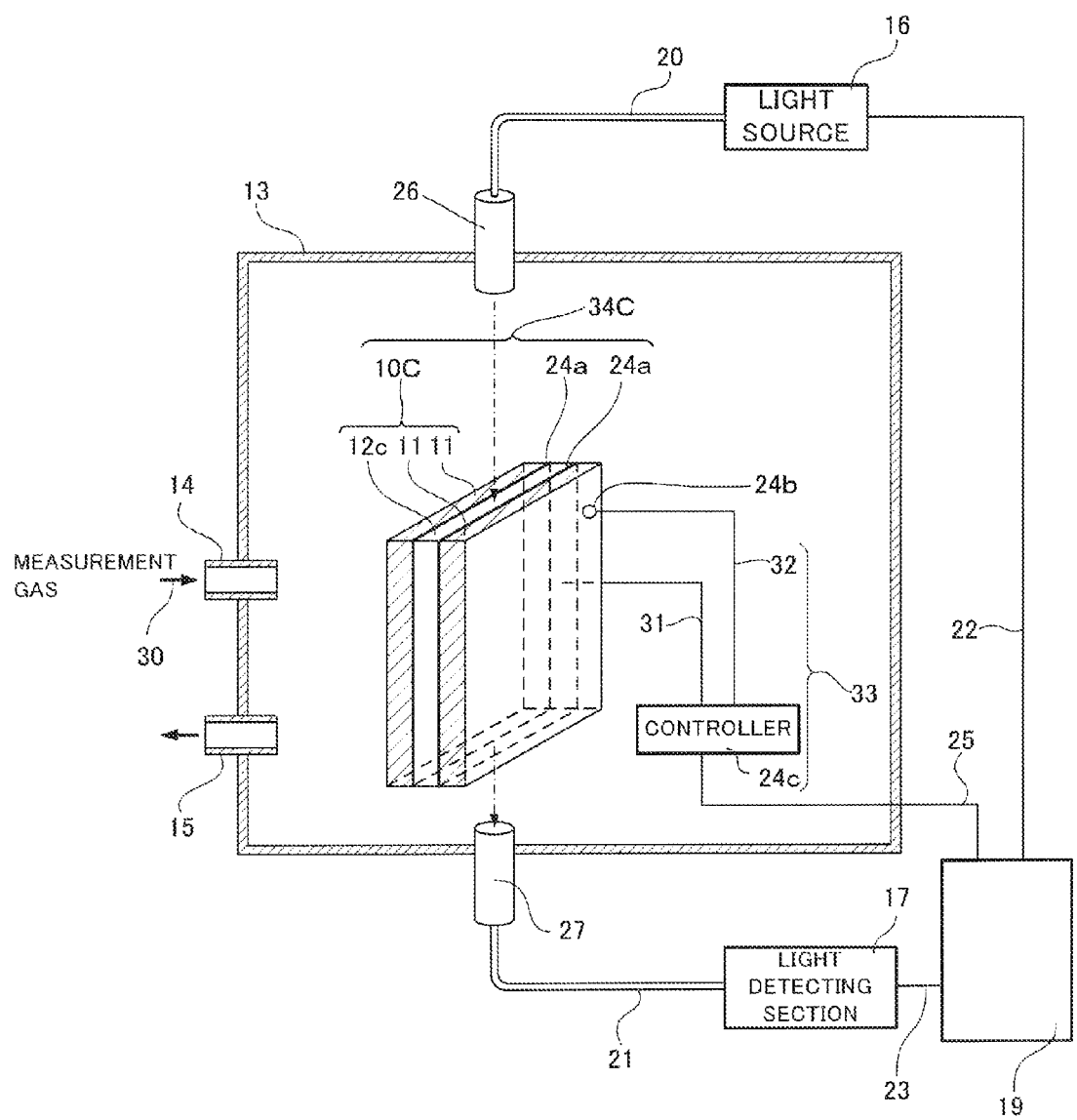
FIG. 21 is a block diagram illustrating a nitrogen oxide concentration determination device using a nitrogen oxide sensor in Embodiment 7 of the present invention.

FIG. 21 illustrates a light waveguide-type nitrogen oxide concentration determination device using a nitrogen oxide sensor 34C of the present invention.

The nitrogen oxide sensor 34C is such that sensing films 11, 11 are formed on both sides of a light-transmitting plate-like substrate 12c. The constitution other than the nitrogen oxide sensor 34C is nearly the same as in Embodiment 6.

A temperature controller 33 allowing the temperature of the nitrogen oxide sensor 34C to get closer to a target temperature is constituted by a temperature sensor 24b such as a thermocouple for sensing the temperatures of heaters 24a, 24a and the like, and a controller 24c for controlling the electrical energization of the heaters 24a, 24a so as to allow a temperature sensed by the temperature sensor 24b to get closer to the target temperature. In the present embodiment, the heaters 24a, 24a are thin film heaters which transmit sensing light and are transparent or nearly transparent, and are disposed between the substrate 12c and the sensing film 11. The temperature sensor 24b is brought into contact with the sensing film 11 and senses the temperature of the sensing film 11.

The heaters 24a, 24a are connected to the controller 24c through a wire 31, and the temperature sensor 24b is connected to the temperature controller 24c through a wire 32. A light source 16, a light detecting section 17 and the temperature controller 24c are connected to a measurement controller 19 through control wires 22, 23 and 25, respectively.

The refractive index n0 of the substrate 12c is 1.4 to 1.5, and the refractive index n1 of the sensing films 11, 11 is 1.5 to 1.8. When the lengthwise end face of the nitrogen oxide sensor 34C is irradiated with diffusion light under such conditions, almost all of the light penetrates from the substrate 12c into the sensing films 11, 11.

In the present embodiment, the end face of the nitrogen oxide sensor 34C is irradiated with diffusion light, but parallel light can also be used. In the case of parallel light, the end face of the nitrogen oxide sensor 34C is obliquely irradiated.

Because the heaters 24a, 24a are thin film heaters which transmit sensing light and are transparent or nearly transparent, as illustrated in a schematic diagram shown in FIG. 10, the light penetrating into the sensing films 11, 11 travels in the sensing films 11, 11, and is reflected on the interfaces between the sensing films 11, 11 and the air, and almost all of the reflected light is reflected on the substrate 12c and the sensing films 11, 11. As described above, the light wave-guided into the sensing films propagates in the sensing films 11, 11 as indicated by the symbol J, and is wave-guided in the films while undergoing multiple reflection on the interfaces between the sensing films and the air and the interfaces between the sensing films and the substrate. In this way, as a result of the multiple reflection, the optical transmittance can be largely reduced, the sensitivity to NO can be increased and thus optical amplification can be performed.

In FIG. 21, the sensing films 11, 11 are formed on both sides of the substrate 12c, but the sensing film 11 may also be formed on only one side. In such a case, the sensitivity to NO is approximately 50% of the sensitivity in the case of FIG. 21.

A method for fabricating the nitrogen oxide sensor 34C is described.

For example, in the same manner as in Embodiment 6, on a glass plate (length: 125 mm, width: 2.5 mm, thickness: 0.7 mm, Eagle 2000, manufactured by Corning Inc.) as the substrate 12c, transparent or nearly transparent thin film heaters are formed as the heaters 24a, 24a.

Next, CoTPP and PEO are added in chloroform to prepare a solution and the solution is stirred to prepare a CoTPP-PEO solution having a CoTPP concentration of $1 \times 10^{-4}$ mol/L and a PEO concentration of 1 (wt/vol) %.

Then, the glass plate on which the thin film heaters have been formed is immersed in the CoTPP-PEO solution for 10 seconds. Then, the substrate is pulled up at an appropriate speed and dried at room temperature. Thus, the nitrogen oxide sensor 34C in which the sensing films 11, 11 are formed on the plate-like substrate 12c is fabricated.

When the sensing film 11 is formed only on one side of the substrate 12c, only the sensing film 11 on the other side may be peeled off after the above-described fabrication, or when coating by immersing is performed, immersion may be performed with the one side covered with a masking tape. In this case, because the heater 24a is transparent or nearly transparent, the heater 24a may be formed either on the sensing film side or on the side on which no sensing film is formed, without any restriction imposed on the placement position.

The procedure of introduction of a measurement gas 30 into a measurement cell 13 and the procedure of the measurement process are the same as in Embodiment 6.

According to the present embodiment, light is repeatedly reflected between the sensing films and the air, the wave guiding in the film is repeated and thus the sensitivity to the NO gas can be increased.

When the end face of the nitrogen oxide sensor 34C is irradiated with parallel light, the incident angle effective for the multiple reflection of waves guided in the film can be set by using an optical prism.

Figure 22:
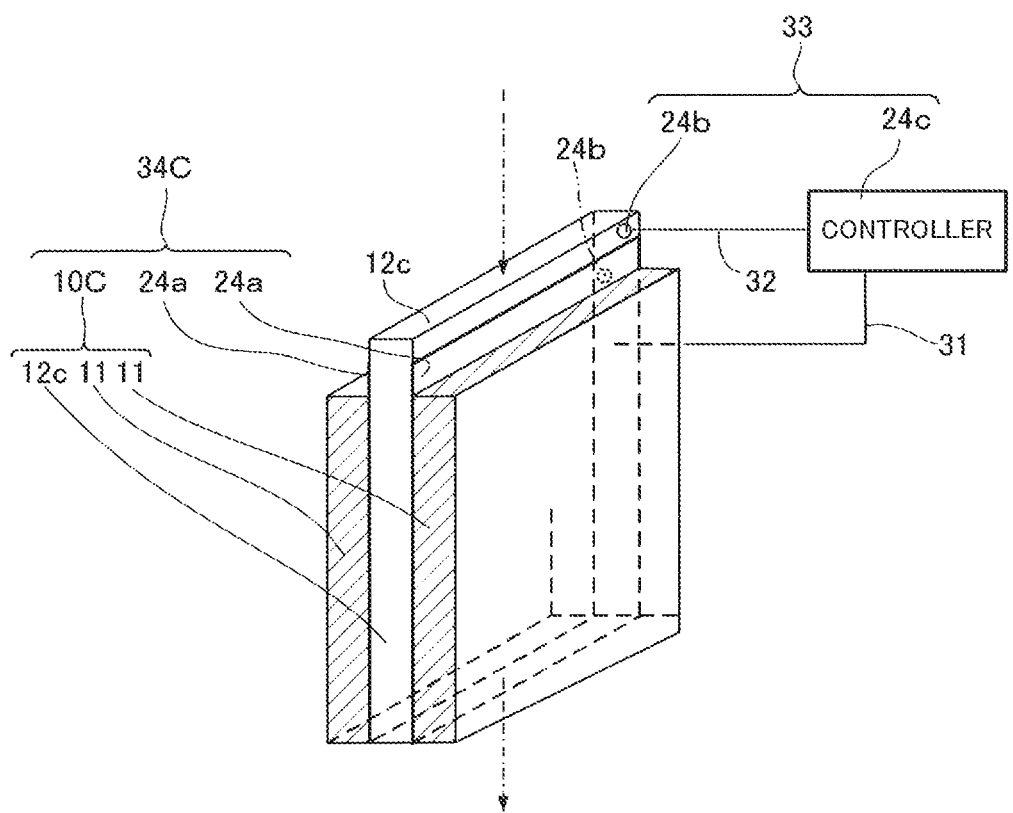
FIG. 22 is an explanatory diagram illustrating another arrangement of a heater 24a and a temperature sensor 24b in the same embodiment.

The sensing film 11 is controlled by the controller 24c to be set at a first or second temperature, T1 or T2, by bringing the temperature sensor 24b into contact with the sensing film 11 to sense the temperature of the sensing film 11; however, as shown in FIG. 22, the temperature sensor 24b is brought into contact with the substrate 12c and thus the temperature of the sensing film 11 may be indirectly sensed to control the temperature of the sensing film 11; or alternatively, as indicated by a broken line in FIG. 22, the temperature sensor 24b is brought into contact with the heater 24a, and thus the temperature of the sensing film 11 may be indirectly sensed to control the temperature of the sensing film 11.

Also in the case of Embodiment 7, the substrate 12c is continuously irradiated with sensing light until the end of measurement; however, when the attenuation of the light due to the sensing film 11 is large, it is necessary to increase the power of light irradiating the substrate 12c; in this case, if continuous light irradiation is performed, heat input into the sensing film 11 or the substrate 12c becomes large, and hence it is preferable to measure the optical signal outputs V1 and V2 by intermittently irradiating the substrate 12c.

Embodiment 8

Figure 23:
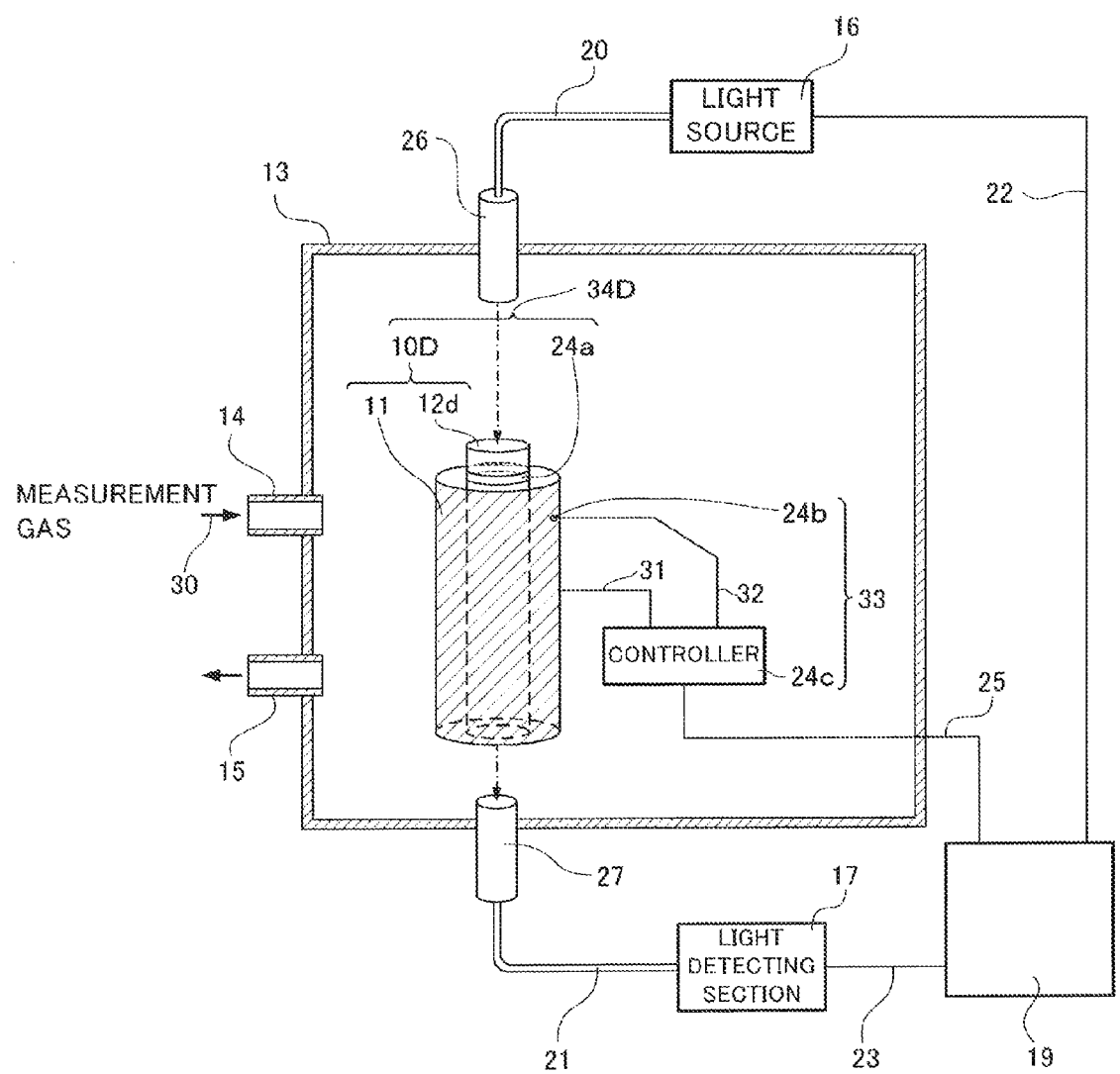
FIG. 23 is a block diagram illustrating a nitrogen oxide concentration determination device using a nitrogen oxide sensor in Embodiment 8 of the present invention.

FIG. 23 illustrates a light waveguide-type nitrogen oxide concentration determination device using a nitrogen oxide sensor 34D of the present invention.

The nitrogen oxide sensor 34C of Embodiment 7 is such that the sensing films are formed on both sides of the plate-like substrate 12c or the sensing film is formed on one side thereof; however, the nitrogen oxide sensor 34D of Embodiment 8 is different from the nitrogen oxide sensor 34C in that the nitrogen oxide sensor 34D is such that a sensing film 11 is formed on the circumference surface of a round rod-like fiber substrate 12d.

A temperature controller 33 allowing the temperature of the nitrogen oxide sensor 34D to get closer to a target temperature is constituted by a temperature sensor 24b such as a thermocouple for sensing the temperature of a heater 24a, and a controller 24c for controlling the electrical energization of the heater 24a so as to allow a temperature sensed by the temperature sensor 24b to get closer to the target temperature. Specifically, the heater 24a is a transparent or nearly transparent thin film heater, and is disposed between the substrate 12d and the sensing film 11.

The temperature sensor 24b is brought into contact with the sensing film 11 and senses the temperature of the sensing film 11. The heater 24a is connected to the controller 24c through a wire 31, and the temperature sensor 24b is connected to the temperature controller 24c through a wire 32. A light source 16, a light detecting section 17 and the temperature controller 24c are connected to a measurement controller 19 through control wires 22, 23 and 25, respectively. The constitution other than the nitrogen oxide sensor 34D is the same as in Embodiment 7.

Because, in the nitrogen oxide sensor 34D, the heater 24a is a thin film heater which transmits sensing light and is transparent or nearly transparent, and the whole surface of the substrate 12d is coated with the sensing film 11, diffusion light introduced to the end face of the substrate 12d is wave-guided in the film in the same manner as in the schematic diagram of FIG. 12, and is reflected on the interface between the sensing film and the air; the reflected light is also reflected on the interface between the substrate 12d and the sensing film 11 and thus multiple reflection is repeated; consequently, the absorption band responding to a NO gas is amplified and thus the sensitivity to NO can be increased. In contrast to the plate-like light waveguide measurement sensor, light leakage from side surfaces does not occur and the light loss can be reduced, so that optical amplification can be performed efficiently, and thus the improvement of the sensitivity to NO can be realized.

The nitrogen oxide sensor 34D is fabricated as follows.

For example, on a glass rod (length: 150 mm, diameter: 3 mm, TE-32, manufactured by Iwaki Glass Co., Ltd.) as the substrate 12d, a transparent or nearly transparent thin film heater is prepared as the heater 24a.

CoTPP and PEO are added in chloroform to prepare a solution and the solution is stirred to prepare a CoTPP-PEO solution having a CoTPP concentration of $1 \times 10^{-4}$ mol/L and a PEO concentration of 1 (wt/vol) %. Next, the glass rod on which the heater 24a has been formed is immersed in the CoTPP-PEO solution for 10 seconds. Then, the substrate is pulled up at an appropriate speed and dried at room temperature.

By the above-described method, a sensor device in which the sensor film 11 is formed on the round rod-like substrate 12d is fabricated. As the substrate, polymer fiber such as polymethyl methacrylate (PMMA) fiber or polycarbonate (PC) fiber can also be used.

The procedure of sensing the nitrogen oxide gas by using the light waveguide-type nitrogen oxide concentration determination device shown in FIG. 23 is the same as in Embodiment 7.

When the end face of the nitrogen oxide sensor 34D is irradiated with diffusion light, the light is repeatedly totally reflected between the substrate 12d and the sensing film 11, and thus the number of times of reflection can be increased. Similarly to the plate-like nitrogen oxide sensor 34A, the nitrogen oxide sensor 34D can largely reduce the optical transmittance, and hence can increase the sensitivity to NO. The round rod-like nitrogen oxide sensor 34D makes it possible to adjust optical components more easily than the plate-like nitrogen oxide sensor 34A.

In the present embodiment, the end face of the nitrogen oxide sensor 34D is irradiated with diffusion light, but parallel light can also be used. In the case of parallel light, the end face of the nitrogen oxide sensor 34D is obliquely irradiated. When the end face of the nitrogen oxide sensor 34D is irradiated with parallel light, the incident angle effective for the multiple reflection of waves guided in the film can be set by using an optical prism.

Figure 24:
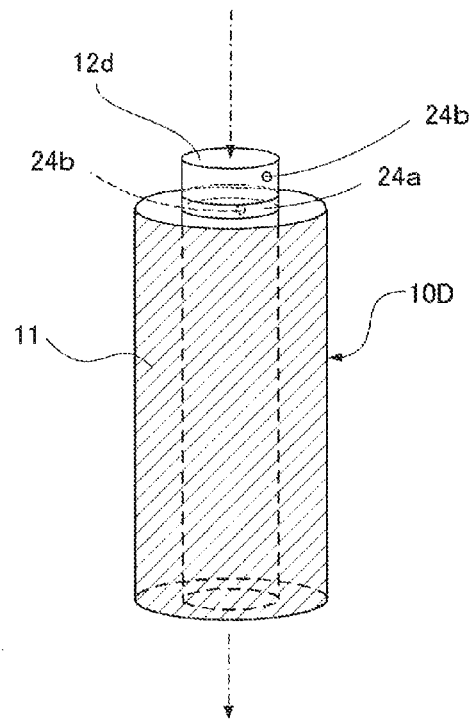
FIG. 24 is an explanatory diagram illustrating another arrangement of a heater 24a and a temperature sensor 24b in the same embodiment.

The temperature of the sensing film 11 is sensed by bringing the temperature sensor 24b into direct contact with the substrate 12d; however, as shown in FIG. 24, the temperature sensor 24b is brought into contact with the substrate 12d and thus the temperature of the sensing film 11 may be indirectly sensed; and, as indicated by a broken line in FIG. 24, the temperature sensor 24b is brought into contact with the heater 24a and the temperature of the sensing film 11 is indirectly sensed, and thus the temperature of the sensing film 11 may also be controlled.

Figure 25:
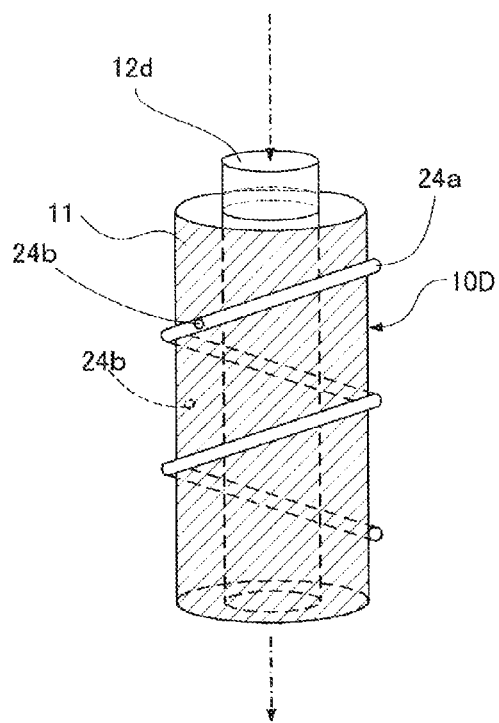
FIG. 25 is an explanatory diagram illustrating yet another arrangement of the heater 24a and the temperature sensor 24b in the same embodiment.

In the above-described nitrogen oxide sensor 34D, the heater 24a is formed between the circumference surface of the round rod-like fiber substrate 12d and the sensing film 11; however, as shown in FIG. 25, even by winding a sheath heater as the heater 24a around the outer surface of the sensing film 11, the sensing film 11 may be set at a first temperature T1 or a second temperature T2. In place of the sheath heater, a NiCr wire or a Pt wire may also be wound. In the case of FIG. 25, the temperature sensor 24b may be placed so as to sense the temperature of the heater 24a, the temperature sensor 24b may be placed so as to directly measure the temperature of the sensing film 11, or the temperature sensor 24b may be placed on the substrate 12d so as to indirectly measure the temperature of the sensing film 11.

Also in the case of Embodiment 8, the substrate 12d is continuously irradiated with sensing light until the end of measurement; however, when the attenuation of the light due to the sensing film 11 is large, it is necessary to increase the power of light irradiating the substrate 12d; in this case, if continuous light irradiation is performed, heat input into the sensing film 11 or the substrate 12d becomes large, and hence it is preferable to measure optical signal outputs V1 and V2 by intermittently irradiating the substrate 12d.

Embodiment 9

Figure 27:
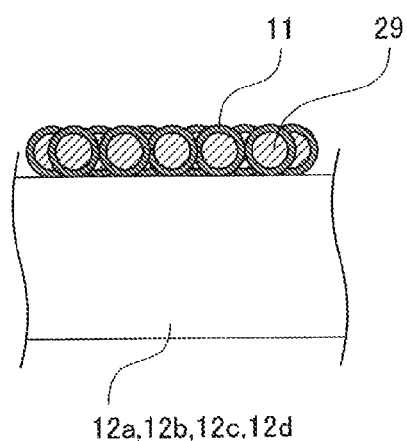
FIG. 27 illustrates the configuration of Embodiment 9 of the present invention.

In each of the above-described embodiments, the sensing film is formed directly on the substrate; however, as shown in FIG. 27, a sensing film 11 is formed on a powder 29 as a carrier, the sensing film including a polymer containing as dispersed therein a porphyrin containing cobalt as a central metal, or a single derivative having a porphyrin skeleton containing cobalt as a central metal or a mixture of derivatives each having a porphyrin skeleton containing cobalt as a central metal, and by forming the powder 29 on the surface of each of substrates 12a, 12b, 12c and 12d, a nitrogen oxide sensing element or a nitrogen oxide sensor may also be fabricated.

Specifically, by making the diameter of the powder 29 smaller than an optical wavelength of 400 nm, the powder becomes transparent with respect to the measurement optical wavelength, and hence the sensing of the nitrogen oxide is made possible.

Here, the case of the powder 29 as a carrier is explained as an example; however, a nanofiber can also be formed as a carrier. In a specific example of formation of a nanofiber as a carrier, a solution in which a porphyrin and a polymer are dissolved is prepared; the solution is injected from a spray nozzle under the condition that a support is placed so as to face the spray nozzle and an electric field is formed between the spray nozzle and the support; thus the solvent is instantly evaporated and consequently, a nanofiber-like sensing film 11 can be formed on the support (electrostatic spray deposition (ESD)). By forming this sensing film on the surface of each of the substrates 12a, 12b, 12c and 12d, a nitrogen oxide sensing element or a nitrogen oxide sensor is fabricated.

Additionally, nonwoven fabric made of a material, for example, cellulose, fluororesin or a biodegradable plastic such as polycaprolactan, polybutylene succinate and polybutylene succinate adipate, is used as a carrier; the nonwoven fabric is immersed in a solution containing a porphyrin and a polymer dissolved therein, and the solvent is dried by evaporation, so that the sensing film 11 is formed on the nonwoven fabric; by forming this sensing film 11 on the surface of each of the substrates 12a, 12b, 12c and 12d, a nitrogen oxide sensing element or a nitrogen oxide sensor is fabricated.

Embodiment 10

The CoTPP-PEO composition dependence of the sensing film 11 in each of the above-described embodiments is investigated.

For the purpose of examining the CoTPP amount in the sensing film which is suitable for the sensing of the NO gas, the following experiments were performed.

As the CoTPP-PEO solution for use in the preparation of the sensing film, solutions which have a PEO concentration of 1 (wt/vol) % and different CoTPP concentrations (the number of moles of CoTPP in relation to the PEO weight (hereinafter referred to as a CoTPP/PEO ratio) are $1 \times 10^{-7}$ mol/g, $1 \times 10^{-6}$ mol/g, $1 \times 10^{-5}$ mol/g, $1 \times 10^{-4}$ mol/g, $1 \times 10^{-3}$ mol/g and $5 \times 10^{-3}$ mol/g) were prepared; each of the resulting solutions was applied onto an alumina substrate 2 by spin coating and was dried; thus, different sensing films in the loads of CoTPP were prepared. The spin coating conditions were such that the spin coating was performed at the same number of rotations and for the same period of time for each of the sensing films. The reactivity to NO of each of the sensing films prepared by the above-described method was evaluated. First, the optical reflection spectrum of each of the sensing films before exposure to the NO gas was measured, and next, each of the sensing films was exposed to the NO gases (base: nitrogen, flow rate: 200 ml/min) having concentrations of 0.01 ppm, 0.1 ppm, 1 ppm and 10 ppm and the resulting changes of the optical reflection spectrum were measured.

Comparative Example 1

In the case of the CoTPP/PEO ratio of $5 \times 10^{-3}$ mol/g, the absorption band having the single central wavelength of 414 nm as shown in FIG. 3 was not obtained; the results were that a superposed band was composed of the absorption band having the central wavelength of 414 nm and the absorption band having the central wavelength of 435 nm; and no reaction with the NO gases having the different NO concentrations was observed. Such persistence of the absorption band having the central wavelength of 435 nm has led to the inference that in a high CoTPP concentration region, a large number of CoTPP molecules are aggregated, the aggregated CoTPP is under the condition that a molecule cannot be bonded to or dissociated form CoTPP, and hence NO cannot be coordination-bonded to CoTPP.

Experimental Example 1

In the case of the CoTPP/PEO ratio of $1 \times 10^{-3}$ mol/g, a large band having the central wavelength of 414 nm was observed, and it was also possible to identify as a subband a band having the central wavelength of 435 nm. The reactivity to the NO gas was evaluated, and the proportional relation was found, in the same manner as in FIG. 7, between the absorbance change and the NO concentration for NO concentrations of 0.01 ppm and 0.1 ppm. However, for NO concentrations of 1 ppm or more, the absorbance change magnitude almost leveled off.

Experimental Example 2

In the cases of the CoTPP/PEO ratios of $1 \times 10^{-5}$ mol/g and $1 \times 10^{-6}$ mol/g, a band having the central wavelength of 414 nm was identified. The reactivity to the NO gas was evaluated, and the approximate proportional relation was found between the absorbance change and the NO concentration for NO concentrations of 1 ppm and 10 ppm. However, in a low NO concentration region, no definite reaction was observed.

Comparative Example 2

In the case of the CoTPP/PEO ratio of $1 \times 10^{-7}$ mol/g, a band having the central wavelength of 414 nm was observed, but the absorbance was small. In the reaction with a NO gas having a concentration of 10 ppm, the reversible reaction between CoTPP and nitrogen monoxide, as shown in FIG. 6, was observed, but no definite reaction with the NO gas in a low concentration range of 1 ppm or less was observed.

From the above-described results, as the NO gas sensor, NO being nitrogen oxide, the number of moles of CoTPP in relation to the weight of PEO in the sensing film is preferably $1 \times 10^{-6}$ mol/g to $1 \times 10^{-3}$ mol/g.

The film thicknesses of the above-described sensing films having different loads of CoTPP were measured, the densities of the films were taken into account, and thus the number of cobalt atoms per unit area was found to fall in a range from $10^{13}$ atoms/cm$^2$ to $10^{16}$ atoms/cm$^2$. Thus, it has been found that the number of cobalt atoms of CoTPP per the unit area of the sensing film is preferably $10^{13}$ atoms/cm$^2$ to $10^{16}$ atoms/cm$^2$.

Experimental Example 3

A description is given on experimental results in the case where a sensing film was composed of a polymer in which a mixture of derivatives each having a porphyrin skeleton containing cobalt as a central metal was dispersed. Chloroform solutions containing mixtures of Co(p-OCH$_3$)TPP and CoTPP were prepared so as to have the sums of Co(p-OCH$_3$)TPP/PEO ratios and CoTPP/PEO ratios of $1 \times 10^{-6}$ mol/g, $1 \times 10^{-5}$ mol/g, $1 \times 10^{-4}$ mol/g and $1 \times 10^{-3}$ mol/g, respectively. Each of the resulting solutions was applied onto the alumina substrate 2 by spin coating and was dried; thus, sensing films were prepared. As the pretreatment of each of the sensors, heat treatment was performed at a first predetermined temperature of 150° C. for 10 minutes, and consequently, a superposed optical absorption band composed of the optical absorption band of Co(II)TPP having a central wavelength of 414 nm and an additional optical absorption band of Co(II)(p-OCH$_3$)TPP having a central wavelength of 419 nm was obtained. Each of the sensing films was exposed to NO gases (base: nitrogen, flow rate: 200 ml/min) having concentrations of 0.01 ppm, 0.1 ppm, 1 ppm and 10 ppm and changes of the optical reflection spectrum were evaluated; and consequently, the superposed optical absorption band was changed to a superposed optical absorption band composed of the optical absorption band of Co(III)TPP having a central wavelength of 435 nm and an additional optical absorption band of Co(III) (p-OCH$_3$)TPP having a central wavelength of 440 nm. Consequently, in the same manner as in the case where the sensing film composed of the PEO polymer in which CoTPP was singly dispersed was formed, there was obtained an approximate proportional relation between the change of the absorbance and the NO concentration, in a NO concentration range including the NO concentrations of 0.01 ppm, 0.1 ppm 1 ppm and 10 ppm. Based on the above-described results, in the sensing film in which a single derivative having a porphyrin skeleton containing cobalt as a central metal or a mixture of derivatives each having a porphyrin skeleton containing cobalt as a central metal was dispersed in a polymer, a wavelength position difference between the optical absorption bands of Co(II) and Co(III) is only about 5 nm, and it has been verified that the nitrogen oxide can be sensed through a band pass filter.

Experimental Example 4

Figure 26:
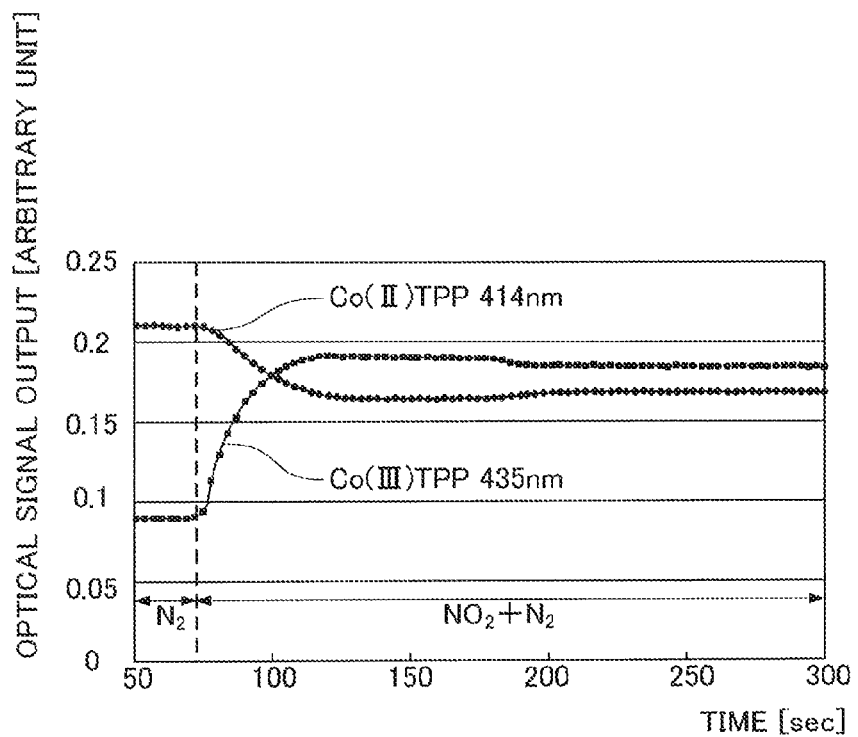
FIG. 26 is an explanatory chart showing absorbances at 414 nm and 435 nm of a nitrogen oxide sensor using a sensing film.

This is an experimental example of sensing of NOx. FIG. 26 shows absorbance measurement results obtained in this experimental example.

Experimental Example 4 presents an example of sensing of a nitrogen dioxide (NO$_2$) gas, using the light reflection-type nitrogen oxide concentration determination device illustrated in FIG. 1. In the light reflection type including the sensing film having a CoTPP/PEO ratio of $1 \times 10^{-5}$ mol/g, the temperature was set at 70° C. after heat treatment, then the NO gas was replaced with the NO$_2$ gas (base: nitrogen, concentration: 10 ppm, flow rate: 200 ml/min) and the NO$_2$ gas was introduced into the measurement cell. At the same time as the introduction of the NO$_2$ gas, in the same manner as in the introduction of the NO gas, the optical absorption band at the wavelength of 414 nm was decreased in intensity, and the optical absorption band at the wavelength of 435 nm was increased in intensity. With the same NOx gas concentration, the response of the sensing film absorption band to the NO$_2$ gas is equal to the response of the sensing film absorption band to the NO gas, and hence the sensing film 11 is effective as the NOx sensor and can be utilized in the environmental measurement of the NOx gas at a level of about 50 ppb.

In Embodiment 5 to Embodiment 9, for the purpose of allowing the temperature of the nitrogen oxide sensor, in specific terms, the temperature of the sensing film 11 to get closer to the intended temperatures T1 and T2, the heater 24a is integrally placed on the substrate, and temperature control is performed by the sensor 24b and the controller 24c; however, in the case where the heater 24a itself is provided with a self-temperature-regulation function, the temperature sensor 24b is not required. An example of such a case is illustrated in FIG. 28.

Figure 28:
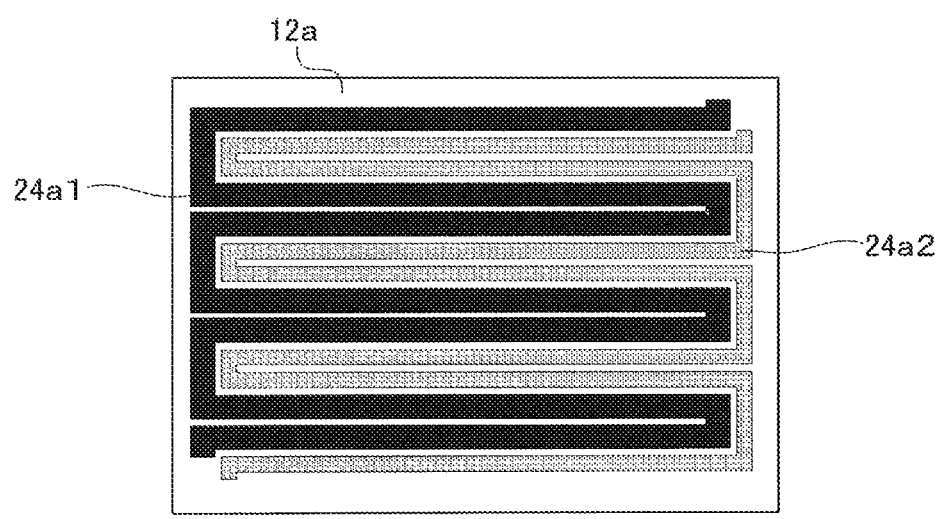
FIG. 28 is a plan view illustrating a temperature controller 33 requiring no separate temperature sensor 24b.

FIG. 28 shows the side opposite to the side on which the sensing film 11 is formed, in the substrate 12a of Embodiment 5. The substrate 12a is provided with a first sheet-like heater 24a1 having PTC (Positive Temperature coefficient) characteristics such that a temperature increase causes an increase in resistance and restricts the electric current flow, and a second sheet-like heater 24a2 having PTC characteristics. Here, the materials and shapes are designed such that the temperature at which the first sheet-like heater 24a1 is stabilized is the first temperature T1 and the temperature at which the second sheet-like heater 24a2 is stabilized is the second temperature T2. As described above, the material quality of the entire first sheet-like heater 24a1 and the material quality of the entire second sheet-like heater 24a2 have temperature sensor functions, and hence the controller 24c in this case does not need the temperature sensor 24b as found in Embodiment 5, due to the constitution in which an electric voltage is applied between both ends of the first sheet-like heater 24a1 during the initialization period of the sensing film 11, and an electric voltage is applied between both ends of the second sheet-like heater 24a2 during a period in which based on the completed initialization of the sensing film 11, the sensing film 11 is exposed to the NO gas (analyte gas). The constitution in which, as described above, the heaters having PTC characteristics are used and the temperature sensor 24b is not required can be embodied also in each of Embodiment 6 to Embodiment 9.

In FIG. 13 and FIG. 18 of Embodiment 5, FIG. 19 and FIG. 20 of Embodiment 6, FIG. 21 and FIG. 22 of Embodiment 7, and FIG. 23 of Embodiment 8, the controller 24c is provided with the control function of allowing the temperature of the nitrogen oxide sensing element to get closer to the target temperature; alternatively, it is also possible to adopt the constitution in which the measurement controller 19 controls the electrical energization of the heater 24a on the basis of the sensed signal of the temperature sensor 24b, so as to allow the temperature of the nitrogen oxide sensing element to get closer to the target temperature.

INDUSTRIAL APPLICABILITY

The nitrogen oxide sensing element and the nitrogen oxide sensor according to the present invention are useful for the sensing of NOx in environmental measurement, medical science, pharmaceutical sciences, bioresearch, drug development, chemical safety assessment and the like.

The invention claimed is:

1. A nitrogen oxide sensing element for sensing a nitrogen monoxide gas in a measurement gas, wherein a sensing film is formed on a surface of a substrate, the sensing film comprising a polymer containing as dispersed therein a porphyrin containing divalent cobalt or in an intermingled manner either divalent cobalt or trivalent cobalt as a central metal, or a single derivative having a porphyrin skeleton containing divalent cobalt or in an intermingled manner either divalent cobalt or trivalent cobalt as a central metal or a mixture of derivatives each having a porphyrin skeleton containing divalent cobalt or in an intermingled manner either divalent cobalt or trivalent cobalt as a central metal.

2. The nitrogen oxide sensing element according to claim 1, wherein the number of moles of the porphyrin containing cobalt as a central metal, or the single derivative having a porphyrin skeleton containing cobalt as a central metal or the mixture of the derivatives each having a porphyrin skeleton containing cobalt as a central metal is $1 \times 10^{-6}$ mol/g to $1 \times 10^{-3}$ mol/g in relation to a unit weight of the polymer in the sensing film.

3. The nitrogen oxide sensing element according to claim 1, wherein the number of cobalt atoms per a unit area of the sensing film is $10^{13}$/cm$^2$ to $10^{16}$/cm$^2$.

4. The nitrogen oxide sensing element according to claim 1, wherein the porphyrin containing cobalt as a central metal is a cobalt tetraphenylporphyrin.

5. The nitrogen oxide sensing element according to claim 1, wherein the substrate is any one of an alumina substrate, a glass substrate, a quartz substrate, a sapphire substrate, a gallium nitride substrate, a plastic substrate, a sheet of paper, a resin, a woven fabric or a nonwoven fabric.

6. The nitrogen oxide sensing element according to claim 1, wherein the polymer is not degraded with respect to a structure thereof by heat reducing the cobalt from trivalent cobalt to divalent cobalt.

7. The nitrogen oxide sensing element according to claim 6, wherein the heat reducing the cobalt from trivalent cobalt to divalent cobalt falls within a range of 50° C. to 200° C.

8. A nitrogen oxide sensing element for sensing a nitrogen monoxide gas in a measurement gas, wherein a carrier comprising a sensing film formed on a surface thereof is supported on a surface of a substrate, the sensing film comprising a polymer containing as dispersed therein a porphyrin containing divalent cobalt or in an intermingled manner either divalent cobalt or trivalent cobalt as a central metal, or a single derivative having a porphyrin skeleton containing divalent cobalt or in an intermingled manner either divalent cobalt or trivalent cobalt as a central metal or a mixture of derivatives each having a porphyrin skeleton containing divalent cobalt or in an intermingled manner either divalent cobalt or trivalent cobalt as a central metal.

9. The nitrogen oxide sensing element according to claim 8, wherein the carrier is a powder or a nanofiber.

10. The nitrogen oxide sensing element according to claim 8, wherein the number of moles of the porphyrin containing cobalt as a central metal, or the single derivative having a porphyrin skeleton containing cobalt as a central metal or the mixture of the derivatives each having a porphyrin skeleton containing cobalt as a central metal is $1 \times 10^{-6}$ mol/g to $1 \times 10^{-3}$ mol/g in relation to a unit weight of the polymer in the sensing film.

11. The nitrogen oxide sensing element according to claim 8, wherein the number of cobalt atoms per a unit area of the sensing film is $10^{13}$/cm$^2$ to $10^{16}$/cm$^2$.

12. The nitrogen oxide sensing element according to claim 8, wherein the porphyrin containing cobalt as a central metal is a cobalt tetraphenylporphyrin.

13. The nitrogen oxide sensing element according to claim 8, wherein the polymer is not degraded with respect to a structure thereof by heat reducing the cobalt from trivalent cobalt to divalent cobalt.

* * * * *

UNITED STATES PATENT AND TRADEMARK OFFICE
CERTIFICATE OF CORRECTION

PATENT NO. : 8,508,738 B2
APPLICATION NO. : 13/131200
DATED : August 13, 2013
INVENTOR(S) : Hiranaka et al.

It is certified that error appears in the above-identified patent and that said Letters Patent is hereby corrected as shown below:

On the Title Page, Item (73) Assignee:    two assignees should be listed.

Panasonic Corporation, Osaka (JP)
        National University Corporation Ehime University, Ehime (JP)

Signed and Sealed this
Twenty-fifth Day of March, 2014

Michelle K. Lee
*Deputy Director of the United States Patent and Trademark Office*